US006084073A

United States Patent [19]
Piatak, Jr.

[11] Patent Number: 6,084,073
[45] Date of Patent: *Jul. 4, 2000

[54] RECOMBINANT RICIN TOXIN

[75] Inventor: Michael Piatak, Jr., Walnut Creek, Calif.

[73] Assignee: Chiron Corporation, Emeryville, Calif.

[*] Notice: This patent is subject to a terminal disclaimer.

[21] Appl. No.: 08/462,167

[22] Filed: Jun. 5, 1995

Related U.S. Application Data

[62] Division of application No. 08/437,048, May 9, 1995, Pat. No. 5,840,522, which is a continuation of application No. 06/837,583, Mar. 7, 1986, abandoned, which is a continuation-in-part of application No. 06/715,934, Mar. 25, 1985, abandoned, which is a continuation-in-part of application No. 06/653,515, Sep. 20, 1994, abandoned.

[51] Int. Cl.⁷ .................. C07K 14/415; C07K 14/42; C12N 15/29

[52] U.S. Cl. .................. 530/370; 530/377; 530/396; 536/23.1; 536/23.6

[58] Field of Search .................. 530/370, 377, 530/396; 536/23.6, 23.1

[56] References Cited

U.S. PATENT DOCUMENTS

| | | | |
|---|---|---|---|
| 4,399,216 | 8/1983 | Axel et al. .................. | 435/6 |
| 4,447,355 | 5/1984 | Sakamoto et al. .................. | 265/112 B |
| 4,457,916 | 7/1984 | Hayashi et al. .................. | 424/101 |
| 4,495,282 | 1/1985 | Ohnishi et al. .................. | 435/68 |
| 4,495,287 | 1/1985 | Uhlin et al. .................. | 435/231 |
| 4,578,355 | 3/1986 | Rosenberg .................. | 435/317 |
| 4,740,461 | 4/1988 | Kaufman .................. | 435/68 |
| 4,946,943 | 8/1990 | Bloch .................. | 530/377 |
| 4,962,189 | 10/1990 | Bloch .................. | 530/391 |
| 5,079,163 | 1/1992 | Piatak, Jr. et al. .................. | 435/252.3 |
| 5,538,868 | 7/1996 | Horn et al. .................. | 435/91.1 |
| 5,622,838 | 4/1997 | Lord et al. .................. | 435/69.1 |

FOREIGN PATENT DOCUMENTS

| | | |
|---|---|---|
| 0 100 641 A2 | 2/1984 | European Pat. Off. . |
| 114 506 A1 | 8/1984 | European Pat. Off. . |
| 0 128 467 A1 | 12/1984 | European Pat. Off. . |
| 0 130 756 A1 | 1/1985 | European Pat. Off. . |
| 0 169 006 A2 | 1/1986 | European Pat. Off. . |
| 0 196 762 A1 | 10/1986 | European Pat. Off. . |
| 0 316 018 A2 | 5/1989 | European Pat. Off. . |
| 1 522 600 | 8/1978 | United Kingdom . |
| 2 106 117 | 4/1983 | United Kingdom . |
| 8319265 | 7/1983 | United Kingdom . |
| 8406569 | 3/1984 | United Kingdom . |
| WO 84/03519 | 9/1984 | WIPO . |
| 145 111 A1 | 6/1985 | WIPO . |
| WO 85/03508 A1 | 8/1985 | WIPO . |
| WO 88/07081 | 9/1988 | WIPO . |

OTHER PUBLICATIONS

A.G. Butterwort et al., "Ricin and Ricin communis Agglutin Subunits are All Deriver from a Single–Size Polypeptide Precursor", Eur. J. Biochem. 137(1–2) 57–65, Dec. 1983.

C.H. Wei et al., "Crystalline Ricin D, a Toxic Anti–Tumor Lectin From Seeds of Ricinus communis", J. Biol. Chem. 253(6): 2061–2066, Mar. 1978.

T. Mise et al., "Isolation and Characterization of Ricin E From Castor Beans", Agric. Biol. Chem. 41(10): 2041–2046, 1978.

J.M. Lord, "Precursors of Ricin and Ricinus communis Agglutinin. Glycosylation and Processing During Synthesis and Intracellular Transport", Eur. J. Biochem. 146(2) 411–416, Jan. 1985.

G. Funatsu et al., "Isolation and Characterization of Two Constituent Polypeptide Chains of Ricin E", Agric. Biol. Chem. 42(4): 851–859, 1978.

E. Saltvedt, "Structure and Toxicity of Pure Ricinus Agglutinin", Biochim. Biophys. Acta 451: 536–548, 1976.

S. Olsnes et al., "Isolation and Comparison of Galactose–Binding Lectins From Abrus precatorius and Ricinus communis", J. Biol. Chem. 249(3): 803–810, Feb. 1974.

Araki and Funatsu, "The Complete Amino Acid Sequence of the B–Chain of Ricin E Isolated from Small Grain Castor Bean Seeds. Ricin E is a Gene Recombination Product of Ricin D and *Ricinus communis* Agglutinin," *Biochimica et Biophysica Acta*, 911:191–200 (1987).

Araki et al., "Revised amino acid sequence of the B–chain of ricin D due to loss of tryptophan in the cyanogen bromide cleavage," *FEBS*, 191(1):121–124 (Oct., 1985).

Arya et al., "Trans–Activator Gene of Human T–Lymphotropic Virus Type III (HTLV–III)," *Science*, 229:69–73 (Jul. 5, 1985).

Bachmann et al., "Linkage Map of *Escheria coli* K–12, Edition 6," *Microbiol. Rev.*, 44(1):1–56 (Mar., 1980).

Banerji et al., "Expression of a β–Globin Gene is Enhanced by Remote SV40 DNA Sequences," *Cell*, 27:299–308 (Dec., 1981).

Bantle et al., "Specificity of oligo (dT)–cellulose chromatography in the isolation of Polyadenylated RNA," *Chemical Abstracts*, 85(5):176 (Aug. 2, 1976) (Abstract 30221v).

Bantle et al., "Specificity of Oligo (dT)–Cellulose Chromatography in the Isolation of polyadenylated RNA," *Anal. Biochem.*, 72(1–2):413–427 (1976).

Bellamy et al., "Recovery and Purification of Nucleic Acids by Means of Cetyltrimethylammonium Bromide," *Methods in Enzymology*, XII, Part B:156–160 (1968).

Bevan et al., "Structure and transcription of the nopaline synthase gene region of T–DNA," *Nucleic Acids Res.*, 11(2):369–385 (1983).

Bittner et al., "Electophoretic Transfer of Proteins and Nucleic Acids from Slab Gels to Diazobenzyloxymethyl Cellulose of Nitrocellulose Sheets," *Ann. Biochem.*, 102:459–471 (1980).

(List continued on next page.)

Primary Examiner—Rebecca E. Prouty
Attorney, Agent, or Firm—Li–Hsien Rin–Laures; Robert P. Blackburn

[57] ABSTRACT

DNA sequences encoding full length precursor proteins, which proteins contain both A and B portions of two ricin isotoxins and ricin agglutinin, as well as the linker regions have been determined. These DNAs or portions or modifications thereof are expressed in recombinant hosts to obtain the desired proteins or proteins which can readily converted thereto. One of the ricin isotoxins may be related to ricin E.

25 Claims, 19 Drawing Sheets

OTHER PUBLICATIONS

Bjorn et al., "Characterization of Translational Inhibitors from *Phytolacca americana*: Amino–Terminal Sequence Determination and Antibody–Inhibitor Conjugates," *Biochim. Biophys. Acta*, 790:154–163 (1984).

Bolivar et al., Construction and Characterization of New Cloning Vehicles II. A Multipurpose Cloning System, *Gene*, 2:95–113 (1977).

Broglie et al., "Structural Analysis of Nuclear Genes Coding for the Precursor to the Small Subunit of Wheat Ribulose–1, 5–Bisphosphate Carboxylase," *Bio/Technology*, 1:55–61 (Mar., 1983).

Carswell et al., "An endotoxin–induced serum factor that causes necrosis of tumors," *Proc. Nat'l Acad. Sci., USA*, 72(9):3666–3670 (Sep., 1975).

Cawley et al., "Homology Between Ricin and *Ricinus communis* Agglutinin: Amino Terminal Sequence Analysis and Protein Synthesis Inhibition Studies," *Arch. Biochem. Biophys.*, 190(2):744–755 (Oct., 1978).

Clewell, D.B., "Nature of Col $E_1$ Plasmid Replication in *Escherichia coli* in the Presence of Chloramphenicol," *J. Bacteriol.*, 110(2):667–676 (May, 1972).

Clewell et al., "Supercoiled Circular DNA–Protein Complex in Escherichia coli: Purification and Induced Conversion to an Open Circular DNA Form," *Proc. Nat'l Acad. Sci., USA*, 62:1159–1166 (1969).

Cohen, S. N., "Nonchromosomal Antibiotic Resistance in Bacteria: Genetic Transformation of *Escherichia coli* by R–Factor DNA," *Proc. Nat'l Acad. Sci., USA*, 69(8):2110–2114 (Aug., 1972).

Cordes and Krohne, "Sequential O–Glycosylation of Nuclear Pore Complex Protein gp62 in Vitro," *Eur. J. Cell. Biol.*, 60:185–195 (1993).

Daubert et al., "Mapping of the Coat Protein Gene of Cauliflower Mosaic Virus by Its Expression in a Prokaryotic System," *Virology*, 122:444–449 (1982).

De Boer et al., "The tac promoter: A functional hybrid derived from the trp and lac promoters," *Proc. Nat'l Acad. Sci., USA*, 80:21–25 (Jan., 1983).

Depicker et al., "Nopaline Synthase: Transcript Mapping and DNA Sequence," *J. Mol. Appl. Genet.*, 1:561–573 (1982).

Derom et al., "High–level synthesis in Escherichia coli of the SV40 small–t antigen under control of the bacteriophage lambda $p_L$ promoter," *Gene*, 17:45–54 (1982).

Edge et al., "Total synthesis of a human leukocyte interferon gene," *Nature*, 292:756–762 (Aug. 20, 1981).

Erlich et al., "Identification of an Antigen–Specific Immunoglobulin M Antibody Associated with Acute Toxoplasma Infection," *Infect. Immun.*, 41(2):683–690 (Aug., 1983).

Fiers et al., "Complete nucleotide sequence of SV40 DNA," *Nature*, 273:113–120 (May 11, 1978).

Funatsu et al., "Primary Structure of Ala Chain of Ricin D," *Agric. Biol. Chem.*, 43(10):2221–2224 (1979).

Funatsu et al., "Separation of the Two Constituent Polypeptide Chains of Ricin D," *Agric. Biol. Chem.*, 41(7):1211–1215 (1977).

Funatsu et al., "Isolation and Characterization of Two Constituent Polypeptide Chains of Ricin E," *Agric. Biol. Chem.*, 42(4):851–859 (1978).

Genaud et al., "Purification of Lectins from *Ricinus communis* by Combination of Affinity and Ion–Exchange Chromatography and Characterization of the Isolated Proteins," *J. Immunol. Methods*, 49:323–332 (1982).

Gerlach et al., "cDNA cloning and induction of the alcohol dehydrogenase gene (Adh1) of maize," *Proc. Nat'l Acad. Sci., USA*, 79:2981–2985 (May, 1982).

Goeddel et al., "Synthesis of human fibroblast interferon by *E. coli*," *Nucleic Acids Res.*, 8(18):4057–4074 (1980).

Goeddel et al., "Human leukocyte interferon produced by *E. coli* is biologically active," *Nature*, 287:411–416 (Oct. 2, 1980).

Gottesman et al., "Retroregulation: Control of Gene Expression from Sites Distal to the Gene," *Cell*, 29: 727–728 (1982).

Graham and van der Eb, "Transformation of Rat Cells by DNA of Human Adenovirus 5," *Virology*, 54:536–539 (1973).

Gray et al., "Periplasmic production of correctly processed human growth hormone in *Escherichia coli*: natural and bacterial signal sequences are interchangeable," *Gene*, 39:247–254 (Jan. 6, 1985).

Grunstein and Hogness, "Colony hybridization: A method for the isolation of cloned DNAs that contain a specific gene," *Proc. Nat'l Acad. Sci., USA*, 72(10):3961–3965 (Oct., 1975).

Gyenes et al., "The use of Affinity Chromatography for the Subfractionation of Polyadenylated RNA on Oligo (dT)–Cellulose," *Proteins Biol. Fluids, Proc. Colloq.*, 23:651–658 (1975).

Haidaris et al., "Serum Containing Tumor Necrosis Factor Is Cytotoxic for the Human Malaria Parasite *Plasmodium falciparum*," *Infect. and Immun.*, 42(1):385–393 (Oct., 1983).

Halling et al., "Genomic cloning and characterization of a ricin gene from *Ricinus communis*," *Nucleic Acids Res.*, 13(22):8019–8033 (1985).

Hess et al., "Cooperation of Glycolytic Enzymes," *J. Adv. Enzyme Reg.*, 7:149–167 (1968).

Holland et al., "Isolation and Identification of Yeast Messenger Ribonucleic Acids Coding for Enolase, Glyceraldehyde–3–phosphate Dehydrogenase, and Phosphoglycerate Kinase," *Biochemistry*, 17:4900–4907 (1978).

Inouye et al., "Signal Sequence of Alkaline Phosphatase of *Escherichia coli*," *J. Bacteriol.*, 149(2):434–439 (Feb., 1982).

Ishiguro et al., "Isolation and Chemical Properties of a Ricin Variant from Castor Bean," *Toxicon.*, 14:157–165 (1976).

Itakura et al., "Expression in Escherichia coli of a Chemically Synthesized Gene for the Hormone Somatosatin," *Science*, 198:1056–1063 (Dec. 9, 1977).

Jay et al., "Chemical Synthesis of a Biologically Active Gene for Human Immune Interferon–γ," *J. Biol. Chem.*, 259(10):6311–6317 (May 25, 1984).

Jay et al., "Construction of a general vector for efficient expression of mammalian proteins in bacteria: Use of a synthetic ribosome binding site," *Proc. Nat'l Acad. Sci., USA*, 78(9):5543–5548 (Sep., 1981).

Jaye et al., "Isolation of a human anti–Hemophilic factor IX cDNA clone using a unique 52–base synthetic oligonucleotide probe deduced from the amino acid sequence of bovine factor IX," *Nucleic Acids Res.*, 11(8):2325–2335 (1983).

Kikuchi et al., "The nucleotide sequence of the promoter and the amino–terminal region of alkaline phosphatase structural gene (phoA) of Escherichia coli," *Nucleic Acids Res.*, 9(21):5671–5678 (1981).

Krens et al., "In vitro transformation of plant protoplasts with Ti–plasmid DNA," *Nature*, 296:72–75 (1982).

Ladin et al., "Characterization of a cDNA encoding ricin E, a hybrid ricin–*Ricinus communis* agglutinin gene from the castor plant *Ricinus communis*," *Plant. Mol. Biol.*, 9:287–295 (1987).

Lamb et al. "Nucleotide sequence of cloned cDNA for preproricin," *Eur. J. Biochem.*, 148:265–270 (1985).

Lin and Li, "Purification and Physiochemical Properties of Ricins and Agglutinins form *Ricinus communis*," *Eur. J. Biochem.*, 105:453–459 (1980).

Maniatis et al., Molecular Cloning: A Laboratory Manual, Cold Spring Harbor Laboratory, pp. 412–413 (1982).

Männel et al., "Macrophages as a Source of Tumoricidal Activity (Tumor–Necrotizing Factor)," *Infect & Immunol.*, 30(2):523–530 (Nov., 1980).

Matteucci et al., "Sythesis of Deoxyoligonucleotides on a Polymer Support," *J. Am. Chem. Soc.*, 103:3185–3191 (1981).

Matthews, N., "Tumour–Necrosis Factor from the Rabbit. V. Synthesis in vitro by Mononuclear Phagocytes from Various Tissues of Normal and BCG–Injected Rabbits," *Brit. J. Cancer*, 44:418–424 (1981).

Maxam et al., "Sequencing End–Labeled DNA with Base–Specific Chemical Cleavages," *Methods in Enzymology*, 65:499–560 (1980).

Meselson et al., "DNA Restriction Enzyme from *E. coli*," *Nature*, 217:1110–1114 (Mar. 23, 1968).

Messing et al., "A system for shotgun DNA sequencing," *Nucleic Acids Res.*, 9(2):308–321 (1981).

Michaelis et al., "In Vitro Construction and Characterization of phoA–lacZ Gene Fusions in *Escherichia coli*," *J. Bact.*, 154(1):356–365 (Apr., 1983).

Mise et al., "Identifications of Tyrosyl Residue Present in the High–affinity Saccharide–binding Site of Ricin D," *Agric. Biol. Chem.*, 50(1):151–155 (1986).

Montfort et al., "The Three–dimensional Structure of Ricin at 2.8 A," *J. Biol. Chem.*, 262(11):5398–5403 (Apr. 15, 1987).

Nambiar et al., "Total Synthesis and Cloning of a Gene Coding for the Ribonuclease S Protein," *Science*, 223:1299–1301 (Mar. 23, 1984).

Nossal and Heppel., "The Release of Enzymes by Osmotic Shock from *Escherichia coli* in Exponential Phase," *J. Biol. Chem.*, 241(13):3055–3062 (Jul. 10, 1966).

Ohsuye et al., "Expression of chemically synthesized α–neo–endorphin gene fused to *E. coli* alkaline phosphatase," *Nucleic Acids Res.*, 11(5):1283–1294 (1983).

Okayama and Berg, "A cDNA Cloning Vector That Permits Expression of cDNA Inserts in Mammalian Cells," *Mol. Cell. Biol.*, 3(2):280–289 (Feb., 1983).

Olsnes et al., "Toxic lectins and related proteins," *Molecular Action of Toxins and Viruses*, Cohen et al., Ed., vol. 2, Elsevier, Amsterdam, pp. 51–105 (1982).

Olsnes et al., "Different Biological Properties of the Two Constituent Peptide Chains of Ricin, a Toxic Protein Inhibiting Protein Synthesis," *Biochemistry*, 12(16):3121–3126 (1973).

Olsnes et al., "Isolation and Comparison of Galactose–binding Lectins from *Abrus precatorius* and *Ricinus communis*," *J. Biol. Chem.*, 249(3):803–810 (Feb. 10, 1974).

Olsnes et al., *Perspectives in Toxicology*, A.W. Bernheimer, Ed., J. Wiley and Sons, New York, pp. 122–147 (1977).

Pennica et al., "Cloning and expression of human tissue–type plasminogen activator cDNA in *E. coli*," *Nature*, 301:214–221 (Jan. 20, 1983).

Pennica et al., "Human tumour necrosis factor: precursor structure, expression and homology to lymphotoxin," *Nature*, 312:724–729 (Dec. 27, 1984).

Piatak et al., "Expression of Soluble and Fully Functional Ricin A Chain in *Escherichia coli* Is Temperature Sensitive," *J. Biol. Chem.*, 263(10):4837–4843 (Apr. 5, 1988).

Robertus et al., "Crystallization of Ricin A Chain Obtained from a Cloned Gene Expressed in *Escherichia coli*," *J. Biol. Chem.*, 262(1):19–20 (Jan. 5, 1987).

Roberts et al., "The Primary Sequence of *Ricinus communis* Agglutinin," *J. Biol. Chem.*, 260(29):15682–15686 (Dec. 15, 1985).

Rutenber et al., "Structure and evolution of ricin B chain," *Nature*, 326:624–626 (Apr. 9, 1987).

Schuler et al., "Closely related families of genes code for the α and α' subunits of the soybean 7S storage protein complex," *Nucleic Acids Res.*, 10(24)8225–8244 (1982).

Shimitake et al., "Purified λ Regulatory Protein cII positively activates promoters for lysogenic development," *Nature*, 292:128–132 (Jul. 9, 1981).

Shirai et al., "Cloning and expression in Escherichia coli of the gene for human tumour necrosis factor," *Nature*, 313:803–806 (Feb. 28, 1985).

Slater et al., "The Purification of Poly(A)–Containing RNA By Affinity Chromatography," *Methods in Molecular Biology*, 2:117–120 (1984).

Starr and Hanover, "Glycosylation of Nuclear Pore Protein p62," *J, Biol. Chem.*, 256(12):6868–6873 (Apr. 25, 1990).

Stinchcomb et al., "Isolation and characterization of a yeast chromosomal replicator," *Nature*, 282:39–43 (Nov. 1, 1979).

Suggs et al., "Use of synthetic oligonucleotides as hybridization probes: Isolation of cloned cDNA sequences for human $β_2$–microglobulin," *Proc. Nat'l Acad. Sci., USA*, 78(11):6613–6617 (Nov., 1981).

Talmadge et al., "Construction of plasmid vectors with unique PstI cloning sites in a signal sequence coding region," *Gene*, 12:235–241 (1980).

Tschumper et al., "Sequence of a yeast DNA fragment containing a chromosomal replicator and the TRP1 gene," *Gene*, 10:157–166 (1980).

Uhlin et al., "Plasmids with Temperature–Dependent Copy Number for Amplification of Cloned Genes and Their Products," *Gene*, 6:91–106 (1979).

Wang et al., "Molecular Cloning of the Complementary DNA for Human Tumor Necrosis Factor," *Science*, 228:149–154 (Apr. 12, 1985).

Wasylyk et al., "The SV40 72 bp Repeat Preferentially Potentiates Transcription Starting from Proximal Natural of Substitute Promoter Elements," *Cell*, 32:503–514 (Feb., 1983).

Wewrzynczak et al., "Amino Acid Residues of Ricin Involved in Galactose–Binding," *J. Cell. Biochem.*, 10B:71 (Feb. 22, 1986) (Abstract G64).

Williamson et al., "Human tumor necrosis factor produced by human B–cell lines synergistic cytotoxic interaction with human interferon," *Proc. Nat'l Acad. Sci., USA*, 80:5397–5401 (Sep., 1983).

Wong et al., "Transcriptional and Translational Start Sites for the *Bacillus thuringiensis* Crystal Protein Gene," *J. Biol. Chem.*, 258(3):1960–1967 (Feb. 10, 1983).

Zoller and Smith, "Laboratory Methods: Oligonucleotide–Directed Mutagenesis: A Simple Method Using Two Oligonucleotide Primers and a Single–Stranded DNA Template," *DNA*, 3(6):479–488 (1984).

Zoller and Smith, "Oligonucleotide–directed mutagenesis using M13–derived vectors: an efficient and general procedure for the production of point mutations in any fragment of DNA," *Nucl. Acids. Res.*, 10(20):6487–6500 (1982).

```
                                                  (HindIII)
                                       (1) ccaagaattgctgcaaaagcttatgaaaccggg
TCTTCCTCAGCTGCTCACTTTCCAATAAAATTCCAAGAATTGCTGCAATCAAAGATGAAACCGGGAGGAAATACT
                                                                  METLysProGlyGlyAsnThr BamH1             (2) ctttcacattagag
ATTGTAATATGGATGTATGCAGTGGCAACATGGCTTTGTTTTGGATCCACCTCAGGGTGGTCTTTCACATTAGAG
IleValIleTrpMETTyrAlaValAlaThrTrpLeuCysPheGlySerThrSerGlyTrpSerPheThrLeuGlu
(HindIIIMET)                                                --- <------(leader) <-----
aagcttatgatattccccaaac
GATAACAACATATTCCCCAAACAATACCCAATTATAAACTTTACCACAGCGGGTGCCACTGTGCAAAGCTACACA
AspAsnAsnIlePheProLysGlnTyrProIleIleAsnPheThrThrAlaGlyAlaThrValGlnSerTyrThr
RTA- <-------IlePheProLysGlnTyrProIleIleAsnPheThrThrAlaGlyAlaThrValGlnSerTyrThr AACTTTATCAGAGCTGTTCGCGGTCGTTTAACAACTGGAGCTGATGTGAGACATGAAATACCAGTGTTGCCAAAC
AsnPheIleArgAlaValArgGlyArgLeuThrThrGlyAlaAspValArgHisGluIleProValLeuProAsn
RTA-AsnPheIleArgAlaValArgGlyArgLeuThrThrGlyAlaAspValArgHisGluIleProValLeuProAsn AGAGTTGGTTTGCCTATAAACCAACGGTTTATTTTAGTTGAACTCTCAAATCATGCAGAGCTTTCTGTTACATTA
ArgValGlyLeuProIleAsnGlnArgPheIleLeuValGluLeuSerAsnHisAlaGluLeuSerValThrLeu
RTA-ArgValGlyLeuProIleAsnGlnArgPheIleLeuValGluLeuGlnAsnHisAlaGluIleSerValThrLeu GCGCTGGATGTCACCAATGCATATGTGGTAGGCTACCGTGCTGGAAATAGCGCATATTTCTTTCATCCTGACAAT
AlaLeuAspValThrAsnAlaTyrValValGlyTyrArgAlaGlyAsnSerAlaTyrPhePheHisProAspAsn
RTA-AlaLeuSerValThrAsnAlaTyrValValGlyTyrArgAlaGlyAsnSerAlaTyrPhePheHisProAspAsn CAGGAAGATGCAGAAGCAATCACTCATCTTTTCACTGATGTTCAAAATCGATATACATTCGCCTTTGGTGGTAAT
GlnGluAspAlaGluAlaIleThrHisLeuPheThrAspValGlnAsnArgTyrThrPheAlaPheGlyGlyAsn
RTA-GlnGluAspAlaGluAlaIleThrHisLeuPheThrAspValGlnAsnArgTyrThrPheAlaPheGlyGlyAsn TATGATAGACTTGAACAACTTGCTGGTAATCTGAGAGAAAATATCGAGTTGGGAAATGGTCCACTAGAGGAGGCT
TyrAspArgLeuGluGlnLeuAlaGlyAsnLeuArgGluAsnIleGluLeuGlyAsnGlyProLeuGluGluAla
RTA-TyrAspArgLeuGluGlnLeuAlaGlyAsnLeuArgGluAsnIleGluLeuGlyAsnGlyProLeuGluGluAla ATCTCAGCGCTTTATTATTACAGTACTGGTGGCACTCAGCTTCCAACTCTGGCTCGTTCCTTTATAATTTGCATC
IleSerAlaLeuTyrTyrTyrSerThrGlyGlyThrGlnLeuProThrLeuAlaArgSerPheIleIleCysIle
RTA-IleSerAlaLeuTyrTyrTyrSerThrGlyGlyThrGlnLeuProThrLeuAlaArgSerPheIleIleCysIle CAAATGATTTCAGAAGCAGCAAGATTCCAATATATTGAGGGAGAAATGCGCACGAGAATTAGGTACAACCGGAGA
GlnMETIleSerGluAlaAlaArgPheGlnTyrIleGluGlyGluMETArgThrArgIleArgTyrAsnArgArg
RTA-GlnMetIleSerGluAlaAlaArgPheGlnTyrIleGluGlyGluMetArgThrArgIleArgTyrAsnArgArg TCTGCACCAGATCCTAGCGTAATTACACTTGAGAATAGTTGGGGGAGACTTTCCACTGCAATTCAAGAGTCTAAC
SerAlaProAspProSerValIleThrLeuGluAsnSerTrpGlyArgLeuSerThrAlaIleGlnGluSerAsn
RTA-SerAlaProAspProSerValIleThrLeuGluAsnSerTrpGlyArgLeuSerThrAlaIleGlnGluSerAsn CAAGGAGCCTTTGCTAGTCCAATTCAACTGCAAAGACGTAATGGTTCCAAATTCAGTGTGTACGATGTGAGTATA
GlnGlyAlaPheAlaSerProIleGlnLeuGlnArgArgAsnGlySerLysPheSerValTyrAspValSerIle
RTA-GlnGlyAlaPheAlaSerProIleGlnLeuGlnArg   AspGlySerLysPheSerValTyrAspValSerIle
                                                                       (TER)
                                                          (3) cacagttttaattgcttataagg
TTAATCCCTATCATAGCTCTCATGGTGTATAGATGCGCACCTCCACCATCGTCACAGTTTTCTTTGCTTATAAGG
LeuIleProIleIleAlaLeuMETValTyrArgCysAlaProProProSerSerGlnPheSerLeuLeuIleArg
RTA-LeuLeuProIleIleAla    MetValTyrArgCysAlaProProProSerSerGlnPhe(<-A-chain)

BamH1
CCAGTGGTACCAAATTTTAATGCTGATGTTTGTATGGATCCTGAGCCCATAGTGCGTATCGTAGGTCGAAATGGT
ProValValProAsnPheAsnAlaAspValCysMETAspProGluProIleValArgIleValGlyArgAsnGly
RTB-        (B-chain-> )AlaAspValCysMetAspProGluProIleValArgIleValGlyArgAsnGly
```

FIG. 1

Estimated Ricin Agglutinin A Sequence

RTA-IlePheProLysGlnTyrProIleIleAsnPheThrThrAlaGlyAlaThrValGlnSerTyrThrAsnPheIle

```
CTGTGCGCAGTCATTTAACAACTGGAGGTGATGTGAGACATGAAATACCAGTGTTGCCAAACAGAGTTGGT
     ValArgSerHisLeuThrThrGlyGlyAspValArgHisGluIleProValLeuProAsnArgValGly
RTA-ArgAlaValArgGlyArgLeuThrThrGlyAlaAspValArgHisGluIleProValLeuProAsnArgValGly

TTGCCTATAAGCCAACGGTTTATTTTAGTTGAACTCTCAAATCATGCAGAGCTTTCTGTTACATTAGCACTGGAT
    LeuProIleSerGlnArgPheIleLeuValGluLeuSerAsnHisAlaGluLeuSerValThrLeuAlaLeuAsp
RTA-LeuProIleAsnGlnArgPheIleLeuValGluLeuGlnAsnHisAlaGluIleSerValThrLeuAlaLeuSer

GTCACCAATGCATATGTGGTCGGCTGCCGCGCTGGAAATAGCGCCTATTTCTTTCATCCTGACAATCAAGAAGAT
    ValThrAsnAlaTyrValValGlyCysArgAlaGlyAsnSerAlaTyrPhePheHisProAspAsnGlnGluAsp
RTA-ValThrAsnAlaTyrValValGlyTyrArgAlaGlyAsnSerAlaTyrPhePheHisProAspAsnGlnGluAsp

GCAGAAGCAATCACTCATCTTTTCACGGATGTTCAAATT?????????????GCTTTTGGTGGTAATTATGATAGA
    AlaGluAlaIleThrHisLeuPheThrAspValGlnIle????????????AlaPheGlyGlyAsnTyrAspArg
RTA-AlaGluAlaIleThrHisLeuPheThrAspValGlnAsnArgTyrThrPheAlaPheGlyGlyAsnTyrAspArg

CTTGAACAACTTG?AGGT    CTTGAGAGAAATATTGAGTTGGGAACTGGTCCATTAGAGGACGCTATCTCAGCG
    LeuGluGlnLeu???Gly    LeuGluArgAsnIleGluLeuGlyThrGlyProLeuGluAspAlaIleSerAla
RTA-LeuGluGlnLeuAlaGlyAsnLeuArgGluAsnIleGluLeuGlyAsnGlyProLeuGluGluAlaIleSerAla

CTTTATTATTATAGTACTTGTGGCACTCAGATTCCAACTCTGGCTCGTTCCTTTATGGTTTGCATCCAAATGATT
    LeuTyrTyrTyrSerThrCysGlyThrGlnIleProThrLeuAlaArgSerPheMETValCysIleGlnMETIle
RTA-LeuTyrTyrTyrSerThrGlyGlyThrGlnLeuProThrLeuAlaArgSerPheIleIleCysIleGlnMetIle

TCAGAAGCAGCAAGATTCCAGTACATTGAGGGAGAAATGCGCACGAGAATTAGGTACAACCGAAGATCTGCACCA
    SerGluAlaAlaArgPheGlnTyrIleGluGlyGluMETArgThrArgIleArgTyrAsnArgArgSerAlaPro
RTA-SerGluAlaAlaArgPheGlnTyrIleGluGlyGluMetArgThrArgIleArgTyrAsnArgArgSerAlaPro

GATCCTAGCGTAATTACACTTGAGAATAGTTGGGGGAGACTTTCCACTGCAATTCAAGAGTCTAACCAAGGAGCC
    AspProSerValIleThrLeuGluAsnSerTrpGlyArgLeuSerThrAlaIleGlnGluSerAsnGlnGlyAla
RTA-AspProSerValIleThrLeuGluAsnSerTrpGlyArgLeuSerThrAlaIleGlnGluSerAsnGlnGlyAla

TTTGCTAGTCCAATTCAACTGCAAAGACGTAACGGTTCCAAATTCAATGTGTACGATGTGAGTATATTAATCCCT
    PheAlaSerProIleGlnLeuGlnArgArgAsnGlySerLysPheAsnValTyrAspValSerIleLeuIlePro
RTA-PheAlaSerProIleGlnLeuGlnArg    AspGlySerLysPheSerValTyrAspValSerIleLeuLeuPro

ATCATAGCTCTCATGGTGTATAGATGCGCACCTCCACCGTCGTCACAGTTTTCTTTGCTTATAAGGCCAGTGGTG
    IleIleAlaLeuMETValTyrArgCysAlaProProProSerSerGlnPheSerLeuLeuIleArgProValVal
RTA-IleIleAla    MetValTyrArgCysAlaProProProSerSerGlnPhe
                                                 (A chain <- )

CCAAATTTTAATGCTGATGTTTGTATGGATCCTGAGCCCATAGTGCGTATCGTAGGTCGAAATGGTCTATGTGTT
    ProAsnPheAsnAlaAspValCysMETAspProGluProIleValArgIleValGlyArgAsnGlyLeuCysVal
RTA-              AlaAspValCysMetAspProGluProIleValArgIleValGlyArgAsnGlyLeuCysVal
                ( -> B chain)

GATGTTACAGGTGAAGAATTC
       AspValThrGlyGluGluPhe
RTB-AsnValArgAspGlyArgPhe
```

This is a composite derived from the inserts of pRTA115 and pRA45.
? = undetermined sequence

FIG. 2

Sequences of pRTA-115, pRTB-4 and pRTB-5 Cloned Inserts

115-TATTAATCCCTATCATAGCTCTCATGGTGTATAGATGCGCACCTCCACCGTCGTCACAGTT

115-TTCTTTGCTTATAAGGCCAGTGGTGCCAAATTTTAATGCTGATGTTTGTATGGATCCTGAGC
                                               115 --(EcoRI)-- 4
115-CCATAGTGCGTATCGTAGGTCGAAATGGTCTATGTGTTGATGTTACAGGTGAAGAATTCTAC
  5-gaattccGCGTATCGTAGGTCGAAATGGTCTATGTGTTGATGTTAGGGATGGAAGATTCCAC 4-GATGGAAACCCAATACAATTGTGGCCTTGCAAATCTAATACAGACTGGAATCAGTTATGGA
  5-AACGGAAACGCAATACAGTTGTGGCCATGCAAGTCTAATACAGATGCAAATCAGCTCTGGA 4-CTTTGAGAAAAGACGGTACAATTCGATCTAATGGCAAGTGTTTGACCATTTATAAGTCCAG
  5-CTTTGAAAAGAGACAATACTATTCGATCTAATGGAAAGTGTTTAACTACTTACGGGTACAG 4-TCTAGGAAAGCATGTGATGATATATAATTGTACTACCGCTACAGTTGGTGCCACCCGTTGG
  5-TCCGGGAGTCTATGTGATGATCTATGATTGCAATACTGCTGCAACTGATGCCACCCGCTGG 4-CAAATATGGGACAACCGAACCATCATAAATCCCATATCTGGTTTAGTTTTGGCAGCCACAT
  5-CAAATATGGGATAATGGAACCATCATAAATCCCAGATCTAGTCTAGTTTTAGCAGCGACAT 4-CAGGAAACAGTGGTACCACACTTACAGTGCAAACCAACATTTATGCCGTTAGTCAAGGTTG
  5-CAGGCAACAGTGGTACCACACTTACAGTGCAAACCAACATTTATGCCGTTAGTCAAGGTTG 4-GCTTCCTAGTAATAATACACAACCTTTTGTGACATCCATTGTTGGGCTAAATGATCTCTGT
  5-GCTTCCTACTAATAATACACAACCTTTTGTGACAACCATTGTTGGGCTATACGGTCTGTGC 4-TTACAAGCAAATACTGGAAAAGTATGGTTAGACGAGTGTACAAGTGAAAAGGCTGAACAAC
  5-TTGCAAGCAAATAGTGGACAAGTATGGATAGAGGACTGTAGCAGTGAAAAGGCTGAACAAC 4-AATGGGCGCTTTATGCAGATGGTTCAATACGGCCTCAGCAAAACCAAGATAACTGCCTTAC
  5-AGTGGGCTCTTTATGCAGATGGTTCAATACGTCCTCAGCAAAACCGAGATAATTGCCTTAC 4-AAGTGATGCTAATATACGAGAAACAATTGTCAAGACCCTCTCTTGCAGCACTGCATCCTCC
  5-AAGTGATTCTAATATACGGGAAACAGTTGTCAAGATCCTCTCTTGTGGCCCTGCATCCTCT 4-GGCCAGCGATGGATGTTCAAGAATGATGGAACCATTTGGAATTTGTATAATGGATTGGTGT
  5-GGCCAACGATGGATGTTCAAGAATGATGGAACCATTTTAAATTTGTATAGTGGGTTGGTGT 4-TAGATGTGAAGCGATCGGATCCGACCCTTAAACAAATCATTATTTACCCTTTCCATGGAAA
  5-TAGATGTGAGGGCATCGGATCCGAGCCTTAAACAAATCATTCTTTACCCTCTCCATGGTGA 4-CCCAAACCAAATATGGTTTCCACTATTTTGATAGACTAATTACCCTCTTGCAGTGTATGTA
  5-CCCAAACCAAATATGGTTACCATTATTTTGATAGACAGATTACTCTCTTGCAGTGTGTATG 4-TGTCCTACCATGAACATAGTTG CTTAAATAAAAAGGACATTGTAAATTAAAAAAA...
  5-    TCCTGCCATGAAAATAGATGGCTTAAATAAAAAGGACATTGTAAATTTTGTAACTGAAA

5-GGACAGCAAGTTATTGCAGTCCAGTATCTAATAAGAGCACAACTATTGTCTTGTGCAAAAAA...

(A) Fusion - pRAP 218

```
     PHOA                    RICIN A
G T G A C A A A G G C G|G C A T T C C C C A A A C A A T A C C C A A T T ---
C A C T G T T T C C G C|C G T A A G G G G T T T G T T A T G G G T T A A ---
V a l T h r L y s A l a A l a P h e P r o L y s G l n T y r P r o I l e ---
                      ↑  ?  ↑
```

(B) Fusion - pRAP 2210

```
        PHOA        RICIN A
G T G A C A A A G G C|G A T C T T C C C C A A A C A A ---
C A C T G T T T C C G C|T A G A A G G G G T T T G T T ---
V a l T h r L y s A l a I l e P h e P r o L y s G l n ---
                      ↑
```

(C) Fusion - pRAP 229

```
 PHOA ──►
V a l T h r L y s A l a I l e S e r L e u T e r
G T G A C A A A G G|C G A T A A G C T T A T G A T A T T C C C C A A A ---
C A C T G T T T C C G C|T A T T C G A A T A C T A T A A G G G G T T T ---
                *                     M e t I l e P h e P r o L y s
                                      ├──► RICIN A
```

```
G T G A C A A A G G|C G C C G A C A C C A G A A A T G ---
C A C T G T T T C C G C|G G C T G T G G T C T T T A C ---
V a l T h r L y s A l a P r o T h r P r o G l u M e t
   (LEADER)          ↑  (NATIVE PROTEIN)
```

REFERENCE - MODIFIED PHOA SEQUENCE (CONTAINING NarI SITE)

↑ = POTENTIAL OR EXPECTED PROCESSING SITE

FIG. 12-1

```
  1 GGATCCACCTCAGGGTGGTCTTTCACATTAGAGGATAACAACATATTCCCCAAACAATAC
    GlySerThrSerGlyTrpSerPheThrLeuGluAspAsnAsnIlePheProLysGlnTyr
    -------------------- leader ------------>||-----> A-chain 61 CCAATTATAAACTTTACCACAGCAGATGCCACTGTGGAAAGCTACACAAACTTTATCAGA
    ProIleIleAsnPheThrThrAlaAspAlaThrValGluSerTyrThrAsnPheIleArg 121 GCTGTGCGCAGTCATTTAACAACTGGAGGTGATGTGAGACATGAAATACCAGTGTTGCCA
    AlaValArgSerHisLeuThrThrGlyGlyAspValArgHisGluIleProValLeuPro 181 AACAGAGTTGGTTTGCCTATAAGCCAACGGTTTATTTTAGTTGAACTCTCAAATCATGCA
    AsnArgValGlyLeuProIleSerGlnArgPheIleLeuValGluLeuSerAsnHisAla 241 GAGCTTTCTGTTACATTAGCACTGGATGTCACCAATGCATATGTGGTCGGCTGCCGCGCT
    GluLeuSerValThrLeuAlaLeuAspValThrAsnAlaTyrValValGlyCysArgAla 301 GGAAATAGCGCCTATTTCTTTCATCCTGACAATCAAGAAGATGCAGAAGCAATCACTCAT
    GlyAsnSerAlaTyrPhePheHisProAspAsnGlnGluAspAlaGluAlaIleThrHis 361 CTTTTCACGGATGTTCAAAATTCATTTACATTCGCCTTTGGTGGTAATTATGATAGACTT
    LeuPheThrAspValGlnAsnSerPheThrPheAlaPheGlyGlyAsnTyrAspArgLeu 421 GAACAACTTGGAGGTCTGAGAGAAAATATTGAGTTGGGAACTGGTCCATTAGAGGACGCT
    GluGlnLeuGlyGlyLeuArgGluAsnIleGluLeuGlyThrGlyProLeuGluAspAla 481 ATCTCAGCGCTTTATTATTATAGTACTTGTGGCACTCAGATTCCAACTCTGGCTCGTTCC
    IleSerAlaLeuTyrTyrTyrSerThrCysGlyThrGlnIleProThrLeuAlaArgSer 541 TTTATGGTTTGCATCCAAATGATTTCAGAAGCAGCAAGATTCCAGTACATTGAGGGAGAA
    PheMetValCysIleGlnMetIleSerGluAlaAlaArgPheGlnTyrIleGluGlyGlu 601 ATGCGCACGAGAATTAGGTACAACCGAAGATCTGCACCAGATCCTAGCGTAATTACACTT
    MetArgThrArgIleArgTyrAsnArgArgSerAlaProAspProSerValIleThrLeu 661 GAGAATAGTTGGGGGAGACTTTCCACTGCAATTCAAGAGTCTAACCAAGGAGCCTTTGCT
    GluAsnSerTrpGlyArgLeuSerThrAlaIleGlnGluSerAsnGlnGlyAlaPheAla 721 AGTCCAATGCAACTGCAAAGACGTAACGGTTCCAAATTCAATGTGTACGATGTGAGTATA
    SerProMetGlnLeuGlnArgArgAsnGlySerLysPheAsnValTyrAspValSerIle 781 TTAATCCCTATCATAGCTCTCATGGTGTATAGATGCGCACCTCCACCGTCGTCACAGTTT
    LeuIleProIleIleAlaLeuMetValTyrArgCysAlaProProSerSerGlnPhe
                                                    A-chain ----->|

841 TCTTTGCTTATAAGGCCAGTGGTGCCAAATTTTAATGCTGATGTTTGTATGGATCCTGAG
    SerLeuLeuIleArgProValValProAsnPheAsnAlaAspValCysMetAspProGlu
                                                    |----> B-chain 901 CCCATAGTGCGTATCGTAGGTCGAAATGGTCTATGTGTTGATGTTACAGGTGAAGAATTC
    ProIleValArgIleValGlyArgAsnGlyLeuCysValAspValThrGlyGluGluPhe 961 TTCGATGGAAACCCAATACAATTGTGGCCTTGCAAATCTAATACAGATTGGAATCAGTTA
    PheAspGlyAsnProIleGlnLeuTrpProCysLysSerAsnThrAspTrpAsnGlnLeu 1021 TGGACTTTGAGAAAAGATAGCACTATTCGATCTAATGGCAAGTGTTTGACCATTTCCAAG
     TrpThrLeuArgLysAspSerThrIleArgSerAsnGlyLysCysLeuThrIleSerLys
```

FIG. 12-2

```
1081 TCCAGTCCAGGACAGCAGGTGGTGATATATAATTGCAGTACCGCTACAGTTGGTGCCACT
     SerSerProGlyGlnGlnValValIleTyrAsnCysSerThrAlaThrValGlyAlaThr

1141 CGTTGGCAAATATGGGACAATCGAACCATCATAAATCCCACATCTGGTCTAGTTTTGGCA
     ArgTrpGlnIleTrpAspAsnArgThrIleIleAsnProThrSerGlyLeuValLeuAla

1201 GCCACATCAGGGAACAGTGGTACCAAACTTACAGTGCAAACCAACATTTATGCCGTTAGT
     AlaThrSerGlyAsnSerGlyThrLysLeuThrValGlnThrAsnIleTyrAlaValSer

1261 CAAGGTTGGCTTCCTACTAATAATACACAACCTTTTGTGACAACCATTGTTGGGCTATAT
     GlnGlyTrpLeuProThrAsnAsnThrGlnProPheValThrThrIleValGlyLeuTyr

1321 GGCATGTGCTTGCAAGCAAATAGTGGAAAAGTATGGTTAGAGGACTGTACCAGTGAAAAG
     GlyMetCysLeuGlnAlaAsnSerGlyLysValTrpLeuGluAspCysThrSerGluLys

1381 GCTGAACAACAATGGGCTCTTTATGCAGATGGTTCAATACGTCCTCAGCAAAACCGCGAT
     AlaGluGlnGlnTrpAlaLeuTyrAlaAspGlySerIleArgProGlnGlnAsnArgAsp

1441 AATTGCCTTACAACTGATGCTAATATAAAAGGAACAGTTGTCAAGATCCTCTCTTGTGGC
     AsnCysLeuThrThrAspAlaAsnIleLysGlyThrValValLysIleLeuSerCysGly

1501 CCTGCATCCTCTGGCCAACGATGGATGTTCAAGAATGATGGAACCATTTTAAATTTGTAT
     ProAlaSerSerGlyGlnArgTrpMetPheLysAsnAspGlyThrIleLeuAsnLeuTyr

1561 AATGGATTGGTGTTAGATGTGAGGCGATCGGATCCGAGCCTTAAACAAATCATTGTTTAC
     AsnGlyLeuValLeuAspValArgArgSerAspProSerLeuLysGlnIleIleValTyr

1621 CCTGTCCATGGAAACCTAAACCAAATATGGTTACCATTATTTTGATAGACAGATTACTCT
     ProValHisGlyAsnLeuAsnGlnIleTrpLeuProLeuPhe......
                                    B-Chain ----->|

1681 CTTGCAGTGTGTATGTCCTGCCATGAAAATAGATGGCTTAAATAAAAAGGACATTGTAAA

1741 TTTTGTAACTGAAAGGACAGCAAGTTATTGCAGTCCAGTATCTAATAAGAGCAGAGCTAT

1801 TGTCTTGTGCATTCTAAAAAAAAAAAAAAAAAAAAAAAAAAAAAAAAAAAAAAAAAAAAA
```

FIG. 13-1

```
  1 XAACCGGGAGGAAATACTATTGTAATATGGATGTATGCAGTGGCAACATGGCTTTGTTTT
      ProGlyGlyAsnThrIleValIleTrpMetTyrAlaValAlaThrTrpLeuCysPhe
    <-------------------------------------------------------------

61 GGATCCACCTCAGGGTGGTCTTTCACATTAGAGGATAACAACATATTCCCCAAACAATAC
    GlySerThrSerGlyTrpSerPheThrLeuGluAspAsnAsnIlePheProLysGlnTyr
    ---------------------------- leader ------>||------>A-chain NH2

121 CCAATTATAAACTTTACCACAGCGGGTGCCACTGTGCAAAGCTACACAAACTTTATCAGA
    ProIleIleAsnPheThrThrAlaGlyAlaThrValGlnSerTyrThrAsnPheIleArg
    end (native)

181 GCTGTTCGCGGTCGTTTAACAACTGGAGCTGATGTGAGACATGAAATACCAGTGTTGCCA
    AlaValArgGlyArgLeuThrThrGlyAlaAspValArgHisGluIleProValLeuPro

241 AACAGAGTTGGTTTGCCTATAAACCAACGGTTTATTTTAGTTGAACTCTCAAATCATGCA
    AsnArgValGlyLeuProIleAsnGlnArgPheIleLeuValGluLeuSerAsnHisAla

301 GAGCTTTCTGTTACATTAGCGCTGGATGTCACCAATGCATATGTGGTAGGCTACCGTGCT
    GluLeuSerValThrLeuAlaLeuAspValThrAsnAlaTyrValValGlyTyrArgAla

361 GGAAATAGCGCATATTTCTTTCATCCTGACAATCAGGAAGATGCAGAAGCAATCACTCAT
    GlyAsnSerAlaTyrPhePheHisProAspAsnGlnGluAspAlaGluAlaIleThrHis
                                                        |ClaI|
421 CTTTTCACTGATGTTCAAAATCGATATACATTCGCCTTTGGTGGTAATTATGATAGACTT
    LeuPheThrAspValGlnAsnArgTyrThrPheAlaPheGlyGlyAsnTyrAspArgLeu

481 GAACAACTTGCTGGTAATCTGAGAGAAAATATCGAGTTGGGAAATGGTCCACTAGAGGAG
    GluGlnLeuAlaGlyAsnLeuArgGluAsnIleGluLeuGlyAsnGlyProLeuGluGlu

541 GCTATCTCAGCGCTTTATTATTACAGTACTGGTGGCACTCAGCTTCCAACTCTGGCTCGT
    AlaIleSerAlaLeuTyrTyrTyrSerThrGlyGlyThrGlnLeuProThrLeuAlaArg

601 TCCTTTATAATTTGCATCCAAATGATTTCAGAAGCAGCAAGATTCCAATATATTGAGGGA
    SerPheIleIleCysIleGlnMetIleSerGluAlaAlaArgPheGlnTyrIleGluGly

661 GAAATGCGCACGAGAATTAGGTACAACCGGAGATCTGCACCAGATCCTAGCGTAATTACA
    GluMetArgThrArgIleArgTyrAsnArgArgSerAlaProAspProSerValIleThr

721 CTTGAGAATAGTTGGGGGAGACTTTCCACTGCAATTCAAGAGTCTAACCAAGGAGCCTTT
    LeuGluAsnSerTrpGlyArgLeuSerThrAlaIleGlnGluSerAsnGlnGlyAlaPhe

781 GCTAGTCCAATTCAACTGCAAAGACGTAATGGTTCCAAATTCAGTGTGTACGATGTGAGT
    AlaSerProIleGlnLeuGlnArgArgAsnGlySerLysPheSerValTyrAspValSer

841 ATATTAATCCCTATCATAGCTCTCATGGTGTATAGATGCGCACCTCCACCATCGTCACAG
    IleLeuIleProIleIleAlaLeuMetValTyrArgCysAlaProProProSerSerGln
                                                        A-chain ----
        ctttgcttataaggagggtggtacc (4)
901 TTTTCTTTGCTTATAAGGCCAGTGGTACCAAATTTTAATGCTGATGTTTGTATGGATCCT
    PheSerLeuLeuIleArgProValValProAsnPheAsnAlaAspValCysMetAspPro
    ->|                                              |----> B-chain 961 GAGCCCATAGTGCGTATCGTAGGTCGAAATGGTCTATGTGTTGATGTTAGGGATGGAAGA
    GluProIleValArgIleValGlyArgAsnGlyLeuCysValAspValArgAspGlyArg 1021 TTCCACAACGGAAACGCAATACAGTTGTGGCCATGCAAGTCTAATACAGATGCAAATCAG
     PheHisAsnGlyAsnAlaIleGlnLeuTrpProCysLysSerAsnThrAspAlaAsnGln
```

FIG. 13-2

```
1081 CTCTGGACTTTGAAAAGAGACAATACTATTCGATCTAATGGAAAGTGTTTAACTACTTAC
     LeuTrpThrLeuLysArgAspAsnThrIleArgSerAsnGlyLysCysLeuThrThrTyr

1141 GGGTACAGTCCGGGAGTCTATGTGATGATCTATGATTGCAATACTGCTGCAACTGATGCC
     GlyTyrSerProGlyValTyrValMetIleTyrAspCysAsnThrAlaAlaThrAspAla

1201 ACCCGCTGGCAAATATGGGATAATGGAACCATCATAAATCCCAGATCTAGTCTAGTTTTA
     ThrArgTrpGlnIleTrpAspAsnGlyThrIleIleAsnProArgSerSerLeuValLeu

1261 GCAGCGACATCAGGGAATAGTGGTACCACACTTACAGTGCAAACCAACATTTATGCCGTT
     AlaAlaThrSerGlyAsnSerGlyThrThrLeuThrValGlnThrAsnIleTyrAlaVal

1321 AGTCAAGGTTGGCTTCCTACTAATAATACACAACCTTTTGTGACAACCATTGTTGGGCTA
     SerGlnGlyTrpLeuProThrAsnAsnThrGlnProPheValThrThrIleValGlyLeu

1381 TATGGTCTGTGCTTGCAAGCAAATAGTGGACAAGTATGGATAGAGGACTGTAGCAGTGAA
     TyrGlyLeuCysLeuGlnAlaAsnSerGlyGlnValTrpIleGluAspCysSerSerGlu

1441 AAGGCTGAACAACAGTGGGCTCTTTATGCAGATGGTTCAATACGTCCTCAGCAAAACCGA
     LysAlaGluGlnGlnTrpAlaLeuTyrAlaAspGlySerIleArgProGlnGlnAsnArg

1501 GATAATTGCCTTACAAGTGATTCTAATATACGGGAAACAGTTGTCAAGATCCTCTCTTGT
     AspAsnCysLeuThrSerAspSerAsnIleArgGluThrValValLysIleLeuSerCys

1561 GGCCCTGCATCCTCTGGCCAACGATGGATGTTCAAGAATGATGGAACCATTTTAAATTTG
     GlyProAlaSerSerGlyGlnArgTrpMetPheLysAsnAspGlyThrIleLeuAsnLeu

1621 TATAGTGGGTTGGTGTTAGATGTGAGGGCATCGGATCCGAGCCTTAAACAAATCATTCTT
     TyrSerGlyLeuValLeuAspValArgAlaSerAspProSerLeuLysGlnIleIleLeu

1681 TACCCTCTCCATGGTGACCCAAACCAAATATGGTTACCATTATTTTGATAGACAGATTAC
     TyrProLeuHisGlyAspProAsnGlnIleTrpLeuProLeuPhe......
                                 B-Chain ----->|

1741 TCTCTTGCAGTGTGTATGTCCTGCCATGAAAATAGATGGCTTAAATAAAAAGGACATTGT

1801 AAATTTTGTAACTGAAAGGACAGCAAGTTATTGCAGTCCAGTATCTAATAAGAGCACAAC

1861 TATTGTCTTGTGCATCTAAAAAAAAAAAAAAAAAAAAAAAAAAAAAAAAAAAAAAAAAAA

1921 AAA
```

FIG. 14-1

```
  1 GGGGGGGGGGGGGATAAAATTCCAAGAATTGCTGCAATCAATATGAAACCGGGAGGAAAT
                                          METLysProGlyGlyAsn
                                          |-----> leader
 61 ACTATTGTAATATGGATGTATGCAGTGGCAACATGGCTTTGTTTTGGATCCACCTCAGGG
    ThrIleValIleTrpMetTyrAlaValAlaThrTrpLeuCysPheGlySerThrSerGly 121 TGGTCTTTCACATTAGAGGATAACAACATATTCCCCAAACAATACCCAATTATAAACTTT
    TrpSerPheThrLeuGluAspAsnAsnIlePheProLysGlnTyrProIleIleAsnPhe
                    leader -----> | |-----> A-chain
181 ACCACAGCGGGTGCCACTGTGCAAAGCTACACAAACTTTATCAGAGCTGTTCGCGGTCGT
    ThrThrAlaGlyAlaThrValGlnSerTyrThrAsnPheIleArgAlaValArgGlyArg 241 TTAACAACTGGAGCTGATGTGAGACATGAAATACCAGTGTTGCCAAACAGAGTTGGTTTG
    LeuThrThrGlyAlaAspValArgHisGluIleProValLeuProAsnArgValGlyLeu 301 CCTATAAACCAACGGTTTATTTTAGTTGAACTCTCAAATCATGCAGAGCTTTCTGTTACA
    ProIleAsnGlnArgPheIleLeuValGluLeuSerAsnHisAlaGluLeuSerValThr 361 TTAGCGCTGGATGTCACCAATGCATATGTGGTCGGCTACCGTGCTGGAAATAGCGCATAT
    LeuAlaLeuAspValThrAsnAlaTyrValValGlyTyrArgAlaGlyAsnSerAlaTyr 421 TTCTTTCATCCTGACAATCAGGAAGATGCAGAAGCAATCACTCATCTTTTCACTGATGTT
    PhePheHisProAspAsnGlnGluAspAlaGluAlaIleThrHisLeuPheThrAspVal 481 CAAAATCGATATACATTCGCCTTTGGTGGTAATTATGATAGACTTGAACAACTTGCTGGT
    GlnAsnArgTyrThrPheAlaPheGlyGlyAsnTyrAspArgLeuGluGlnLeuAlaGly 541 AATCTGAGAGAAAATATCGAGTTGGGAAATGGTCCACTAGAGGAGGCTATCTCAGCGCTT
    AsnLeuArgGluAsnIleGluLeuGlyAsnGlyProLeuGluGluAlaIleSerAlaLeu 601 TATTATTACAGTACTGGTGGCACTCAGCTTCCAACTCTGGCTCGTTCCTTTATAATTTGC
    TyrTyrTyrSerThrGlyGlyThrGlnLeuProThrLeuAlaArgSerPheIleIleCys 661 ATCCAAATGATTTCAGAAGCAGCAAGATTCCAATATATCGAGGGAGAAATGCGCACGAGA
    IleGlnMetIleSerGluAlaAlaArgPheGlnTyrIleGluGlyGluMetArgThrArg 721 ATTAGGTACAACCGGAGATCTGCACCAGATCCTAGCGTAATTACACTTGAGAATAGTTGG
    IleArgTyrAsnArgArgSerAlaProAspProSerValIleThrLeuGluAsnSerTrp 781 GGGAGACTTTCCACTGCAATTCAAGAGTCTAACCAAGGAGCCTTTGCTAGTCCAATTCAA
    GlyArgLeuSerThrAlaIleGlnGluSerAsnGlnGlyAlaPheAlaSerProIleGln 841 CTGCAAAGACGTAATGGTTCCAAATTCAGTGTGTACGATGTGAGTATATTAATCCCTATC
    LeuGlnArgArgAsnGlySerLysPheSerValTyrAspValSerIleLeuIleProIle
                                            cgtcacagttttgattgcttata
901 ATAGCTCTCATGGTGTATAGATGCGCACCTCCACCATCGTCACAGTTTTCTTTGCTTATA
    IleAlaLeuMetValTyrArgCysAlaProProProSerSerGlnPheSerLeuLeuIle
                                               A-chain -----> |
      aggccagtggtaccaaattttatggctgatgtttg (5)
961 AGGCCAGTGGTACCAAATTTTAATGCTGATGTTTGTATGGATCCTGAGCCCATAGTGCGT
    ArgProValValProAsnPheAsnAlaAspValCysMetAspProGluProIleValArg
                                        |-----> B-chain
1021 ATCGTAGGTCGAAATGGTCTATGTGTTGATGTTAGGGATGGAAGATTCCACAACGGAAAC
     IleValGlyArgAsnGlyLeuCysValAspValArgAspGlyArgPheHisAsnGlyAsn
```

FIG. 14-2

```
1081 GCAATACAGTTGTGGCCATGCAAGTCTAATACAGATGCAAATCAGCTCTGGACTTTGAAA
     AlaIleGlnLeuTrpProCysLysSerAsnThrAspAlaAsnGlnLeuTrpThrLeuLys

1141 AGAGACAATACTATTCGATCTAATGGAAAGTGTTTAACTACTTACGGGTACAGTCCGGGA
     ArgAspAsnThrIleArgSerAsnGlyLysCysLeuThrThrTyrGlyTyrSerProGly

1201 GTCTATGTGATGATCTATGATTGCAATACTGCTGCAACTGATGCCACCCGCTGGCAAATA
     ValTyrValMetIleTyrAspCysAsnThrAlaAlaThrAspAlaThrArgTrpGlnIle

1261 TGGGATAATGGAACCATCATAAATCCCAGATCTAGTCTAGTTTTAGCAGCGACATCAGGG
     TrpAspAsnGlyThrIleIleAsnProArgSerSerLeuValLeuAlaAlaThrSerGly

1321 AACAGTGGTACCACACTTACAGTGCAAACCAACATTTATGCCGTTAGTCAAGGTTGGCTT
     AsnSerGlyThrThrLeuThrValGlnThrAsnIleTyrAlaValSerGlnGlyTrpLeu

1381 CCTACTAATAATACACAACCTTTTGTGACAACCATTGTTGGGCTATATGGTATGTGCTTG
     ProThrAsnAsnThrGlnProPheValThrThrIleValGlyLeuTyrGlyMetCysLeu

1441 CAAGCAAATAGTGGAAAAGTATGGTTAGAGGACTGTACCAGTGAAAAGGCTGAACAACAA
     GlnAlaAsnSerGlyLysValTrpLeuGluAspCysThrSerGluLysAlaGluGlnGln

1501 TGGGCTCTTTATGCAGATGGTTCAATACGTCCTCAGCAAAACCGCGATAATTGCCTTACA
     TrpAlaLeuTyrAlaAspGlySerIleArgProGlnGlnAsnArgAspAsnCysLeuThr

1561 ACTGATGCTAATATAAAAGGAACAGTTGTCAAGATCCTCTCTTGTGGCCCTGCATCCTCT
     ThrAspAlaAsnIleLysGlyThrValValLysIleLeuSerCysGlyProAlaSerSer

1621 GGCCAACGATGGATGTTCAAGAATGATGGAACCATTTTAAATTTGTATAATGGATTGGTG
     GlyGlnArgTrpMetPheLysAsnAspGlyThrIleLeuAsnLeuTyrAsnGlyLeuVal

1681 TTAGATGTGAGGCGATCGGATCCGAGCCTTAAACAAATCATTGTTCACCCTTTCCATGGA
     LeuAspValArgArgSerAspProSerLeuLysGlnIleIleValHisProPheHisGly

1741 AACCTAAACCAAATATGGTTACCATTATTTTGATAGACAGATTACTCTCTTGCAGTGTGT
     AsnLeuAsnGlnIleTrpLeuProLeuPhe......
                     B-Chain ----->|

1801 ATGTCCTGCCATGAAATAGATGGCTTAAATAAAAAGGACATTGTAAATTTTGTAACTGAA

1861 AGGACAGCAAGTTATTCGAGCTCAGTATCTAATAAGAGCACAACTATTGTCTTGTGCAAA

1921 AAAAAAAAAAAAAAAAAAAAAAAAA
```

FIG. 15

```
                (MK)
RICIN D     <PGGNTIVIWMYAVATWLCFGSTSGWSFTLEDNNIFPKQYPIINFTTAGATVQSYTNF
RICIN E   MK<PGGNTIVIWMYAVATWLCFGSTSGWSFTLEDNNIFPKQYPIINFTTAGATVQSYTNF
                       LEADER <—|—> A-CHAIN

Seq D:    IRAVRGRLTTGADVRHEIPVLPNRVGLPINQRFILVELSNHAELSVTLALDVTNAYVVGY
Seq E:    IRAVRGRLTTGADVRHEIPVLPNRVGLPINQRFILVELSNHAELSVTLALDVTNAYVVGY

Seq D:    RAGNSAYFFHPDNQEDAEAITHLFTDVQNRYTFAFGGNYDRLEQLAGNLRENIELGNGPL
Seq E:    RAGNSAYFFHPDNQEDAEAITHLFTDVQNRYTFAFGGNYDRLEQLAGNLRENIELGNGPL

Seq D:    EEAISALYYYSTGGTQLPTLARSFIICIQMISEAARFQYIEGEMRTRIRYNRRSAPDPSV
Seq E:    EEAISALYYYSTGGTQLPTLARSFIICIQMISEAARFQYIEGEMRTRIRYNRRSAPDPSV

Seq D:    ITLENSWGRLSTAIQESNQGAFASPIQLQRRNGSKFSVYDVSILIPIIALMVYRCAPPPS
Seq E:    ITLENSWGRLSTAIQESNQGAFASPIQLQRRNGSKFSVYDVSILIPIIALMVYRCAPPPS
                                                           A-CHAIN <—

Seq D:    SQFSLLIRPVVPNFNADVCMDPEPIVRIVGRNGLCVDVRDGRFHNGNAIQLWPCKSNTDA
Seq E:    SQFSLLIRPVVPNFNADVCMDPEPIVRIVGRNGLCVDVRDGRFHNGNAIQLWPCKSNTDA
           —|            |—> B-CHAIN

Seq D:    NQLWTLKRDNTIRSNGKCLTTYGYSPGVYVMIYDCNTAATDATRWQIWDNGTIINPRSSL
Seq E:    NQLWTLKRDNTIRSNGKCLTTYGYSPGVYVMIYDCNTAATDATRWQIWDNGTIINPRSSL

*       *  *  *
Seq D:    VLAATSGNSGTTLTVQTNIYAVSQGWLPTNNTQPFVTTIVGLYGLCLQANSGQVWIEDCS
Seq E:    VLAATSGNSGTTLTVQTNIYAVSQGWLPTNNTQPFVTTIVGLYGMCLQANSGKVWLEDCT

*   *  **
Seq D:    SEKAEQQWALYADGSIRPQQNRDNCLTSDSNIRETVVKILSCGPASSGQRWMFKNDGTIL
Seq E:    SEKAEQQWALYADGSIRPQQNRDNCLTTDANIKGTVVKILSCGPASSGQRWMFKNDGTIL

*       *      **  **
Seq D:    NLYSGLVLDVRASDPSLKQIILYPLHGDPNQIWLPLF>
Seq E:    NLYNGLVLDVRRSDPSLKQIIVHPFHGNLNQIWLPLF>
```

RECOMBINANT RICIN TOXIN

This application is a divisional of application Ser. No. 06/837,583, filed Mar. 7, 1986.

This is a divisional of U.S. Ser. No. 08/437,048, filed May 9, 1995, now U.S. Pat. No. 5,840,522, which is a continuation of U.S. Ser. No. 06/837,583, filed Mar. 7, 1986, now abandoned, which is a continuation-in-part of U.S. Ser. No. 06/715,934, filed Mar. 25, 1985, now abandoned, which is a continuation-in-part of U.S. Ser. No. 06/653,515, filed Sep. 20, 1984, now abandoned.

TECHNICAL FIELD

This invention relates to the production of toxin fragments using recombinant technology. More specifically, the invention relates to producing ricin toxin proteins using recombinant means.

BACKGROUND ART

Ricin toxin (RT or ricin) is a naturally occurring toxin composed of an enzymatically active, cytotoxic "A" amino acid sequence, and a "B" sequence, which is presumed to be responsible both for attaching the "A" sequence to a target cell to be killed, and to aid in the translocation of A fragment into the cytoplasm. Other examples of such toxins include diphtheria toxin and the exotoxin from *Pseudomonas aeruginosa*. Other toxic proteins, such as, for example, those derived from *Phytolacca americana* (PAPI, PAPII, and PAP-S) and gelonin show in vitro activities comparable to the "A" sequences of the above toxins, but are inactive in vivo, presumably due to the absence of a "B" chain.

The "ricin" peptides of the present invention are derived from the seeds of *Ricinus communis*, commonly known as castor beans. Two similar proteins (often called lectins) are extractable from these seeds: the above-mentioned ricin and *Ricin communis* agglutinin (RCA). Both proteins contain A and B portions which do not comprise a single peptide but are joined by a disulfide link. The A portions of both ricin and RCA are capable of catalytically inactivating the large subunit of ribosomes in vitro and the mechanism of ricin for in vivo cytotoxicity is believed to reside in this capacity for ribosome inactivation. Ricin and RCA appear to be highly homologous but differences exist. RCA is dramatically less toxic, and appears to exhibit characteristics corresponding to those expected of a dimer of ricin.

Careful fractionation of castor bean extracts shows the presence of several ricin isotoxins. The distinction between ricins D and E has been previously disclosed (Mise, et al, *Agric Biol Chem* (1977) 41:2041–2046; Wei, et al, *J Biol Chem* (1978) 253:2061–2066: Lin, et al, *Eur J Biochem* (1980) 105:453–459; Genaud, et al, *J Immunol Meth* (1982) 49:323–332). Ricin D has a pI near 7.4 and a high affinity for agarose; ricin E has a pI near 8.8 and a low affinity for agarose. There are several reports of purported isotoxins which have been shown to be more acidic forms of ricin D (Olsnes, et al, *J Biol Chem* (1974) 249:803–810; Ishiguro, et al, *Toxicon* (1976) 14:157–165; Cawley, et al, *Arch Biochem Biophys* (1978) 190:744–755).

The differences in properties between ricins D and E seem to reside in the B chain (Funatsu, et al, *Agric Biol Chem* (1978) 42:851–859). The RTA chains from ricins D and E are identical in composition, pI, and apparent molecular weight. However, ricin D yields two distinct RTA species, RTA1 and RTA2. These isoenzymes differ in molecular weight by SDS-PAGE and in carbohydrate content, and can be resolved by ion exchange chromatography with a very shallow salt gradient (Olsnes, et al, *Biochemistry* (1973) 12:3121–3126).

U.S. patent application Ser. No. 747,114, filed Jun. 20, 1985, assigned to the same assignee and incorporated herein by reference discloses the separation of an additional and previously unreported ricin E isotoxin. For convenience, the ribotoxin most similar to the previous ricin E preparation was designated ricin El, and the novel ribotoxin was designated ricin E2. Ricin E2 has a pI identical to that of ricin E1. Compared to ricin E1, it is 1% as toxic to mice and 2–4% as toxic to cultured cell lines, is bound to agarose more tightly at moderate to high ionic strength, and is approximately 2 kD larger by SDS-PAGE.

The components of ricin and of RCA have been well characterized on the basis of the extracted materials, and their properties extensively reviewed: Olsnes, S., *Perspectives in Toxicology*, A. W. Bernheimer, Ed (1977) J. Wiley & Sons, NY, pp 122–147; Olsnes, S., et al, *Molecular Action of Toxins and Viruses*, Cohen, et al, Ed (1982) Elsevier, Amsterdam, pp 51–105. Ricin has an apparent molecular weight of 58,000 daltons and consists of the A chain with a molecular weight of 32,000 daltons and a B chain of molecular weight of 34,700 daltons. RCA is a tetramer which has two A subunits of molecular weight 32,000, and two B subunits of molecular weight 36,000 each. In their native environments, the A and B chains are generally glycosylated. The A and B subunits of both ricin and RCA are linked only by a single disulfide bond, and not by peptide linkage unlike, for example diphtheria toxin which is found as a single chain peptide. It is also known that both ricin and RCA, though having separate peptides for A and B portions, are each derived from a single chain precursor in each case (Butterworth, H. E., et al, *Eur J Biochem* (1983) 137:57). This precursor was shown to contain a sequence of 12 amino acids between the A chain (amino terminal) and B chain (carboxy terminal) sequence; U.S. Ser. No. 578,121, filed Feb. 8, 1984, assigned to the same assignee and incorporated herein by reference. The invention hereinbelow shows the ricin A sequence to contain 265 amino acids preceded by a 35 amino acid leader (signal) peptide. It is assumed that upon excision of the dodecameric intervening peptide, the A and B chains remain linked through the single disulfide bond.

With regard to the invention herein, three full-length ricin related clones have been isolated, two of which correspond to proteins of known sequence. The insert for pRT3 corresponds in the amino acid sequence encoded to the primary sequence of ricin agglutinin. The cDNA insert in pRT17 corresponds to the composite between the ricin toxin B chain encoded in the DNA disclosed in U.S. Ser. No. 578,121 (supra) and the ricin A encoding sequences described herein. This is the DNA, then, encoding the precursor for ricin D.

pRT38, on the other hand, encodes a new protein which, because of the predicted characteristics of the deduced protein in comparison to ricin D is presumed to be the DNA encoding ricin E. Specifically, ricin E has a pI considerably higher than that of ricin D, as disclosed above, therefore the deviations from homology which comprise changes from amino acids in ricin D neutral to basic amino acids in the new protein are consistent with this identification of the protein encoded.

The present invention provides a means for obtaining the A chain of ricin and the full length "precursor" chains of two ricin isotoxins and of RCA using recombinant technology. Native ricin A and native ricin exist in a number of homologous but not exactly identical forms depending on the plant variety used as source, but even protein derived from a single plant may exhibit more than one primary structure. Recombinantly produced ricin A, of course, permits production of a single desired amino acid sequence, and makes possible an exploration of the structural-features required for its activity. The techniques and materials of the present invention further permit selective modification of the amino acid sequence of the proteins and thus permit manipulation to provide properties which are capable of tailoring the cytotoxicity and other properties of these materials. The production of recombinant ricin B chain has been disclosed in U.S. Ser. No. 578,121 (supra). The invention herein, by enabling the production of ricin A and of full length ricin using predictable, efficient, and economic procedures which, further, permit directed modification, permits the use of these proteins in practical and improved ways not before possible. Further, by suitable recombinant manipulation employing, as well, the DNA sequence encoding B chain, the full length ricin toxin may be cloned and expressed and various hybrids containing portions of the several proteins may be obtained.

In addition, by using a novel construct employing codons for the leader sequence of a bacterial secreted protein, soluble biologically active ricin A chain and ricin precursor are directly obtained using procaryotic hosts, without need for further treatment to refold or solubilize the heterologous protein.

DISCLOSURE OF THE INVENTION

The invention relates, in one aspect, to the various ricin moieties and, in particular, to soluble, biologically active proteins which are prepared using recombinant techniques. The amino acid sequence of the ricin A, ricin or RCA can be, if desired, absolutely identical to the ricin A, ricin or RCA peptide amino acid sequence as extracted from a particular sample of castor bean seeds, but the recombinant product is inevitably somewhat modified due to the environment of its production, and may be further modified at the will of the producer to contain alterations in amino acid sequence or in the level of glycosylation.

For ricin A, for example, when produced by procaryotes such as E. coli MC1000 lambda lysogen under the compatible $P_L$ promoter control, the ricin A requires solubilization by, for example, detergents or chaotropic agents in order to apply suitable purification methods. Certain constructions of the invention, however, in appropriate hosts result directly in soluble ricin A which requires no further treatment to be subjected to purification and to display cytotoxicity. Such soluble ricin A may be extracted from the host cell using normal mechanical disruption and purified. Accordingly, one aspect of the invention relates to methods and materials for production of ricin A, and for production of other ricin related proteins by recombinant techniques, and to the forms so produced.

In other aspects, the invention relates to expression systems which are capable of effecting the expression of these proteins and of ricin A, to host cells which have been transformed with such systems, and to cultures thereof; as well as to modified DNA sequences encoding ricin A and ricin and their precursors; and to expression sequences for such ricin related fragments whether modified or not. Specifically, aspects of the invention relate to soluble recombinant ricin A with cytotoxic activity and to materials and methods for its production.

The invention also relates to a novel protein having the amino acid sequence of ricin E, to the ricin B portion thereof, and to recombinant materials useful for its production.

It has also been found that phenyl sepharose can be used to ease soluble recombinant ricin A from cellular materials with which it is associated, and an additional aspect of the invention is directed to this technique.

BRIEF DESCRIPTION OF THE DRAWINGS

FIG. 1 shows the complete sequence of the cloned insert of pRA123 which encodes the entire RTA protein. Also shown are the corresponding protein sequence of ricin A as deduced, the sequence of an isolated, native RTA, and, as well, the portions of the nucleotide sequence modified by primer directed mutagenesis.

FIG. 2 shows a composite of the nucleotide sequences of the cDNA inserts in the plasmids pRTA115 and pRA45 corresponding to the RCA-A chain coding sequence, the amino acid sequence deduced from it, and the sequence of native RTA.

FIG. 4 shows the nucleotide sequences of three plasmids containing CDNA inserts obtained by probing a CDNA library for sequences encoding ricin B.

FIGS. 5A and 5B shows the 5' sequences of the phoA operon, and modification to place a NarI site at the C-terminus of the leader.

FIG. 9 shows the junction regions of the plasmids illustrated in FIGS. 7 and 8.

FIGS. 12-1 and 12-2 shows the DNA and deduced amino acid sequence for the RCA encoding insert of pRT3.

FIGS. 13-1 and 13-2 shows the DNA and deduced amino acid sequence for the ricin D encoding insert of pRT17.

FIGS. 14-1 and 14-2 shows the DNA and deduced amino acid sequence for the ricin E encoding insert of pRT38.

FIG. 15 shows a comparison of the amino acid sequence encoded by pRT17 and pRT38.

Figure 3:
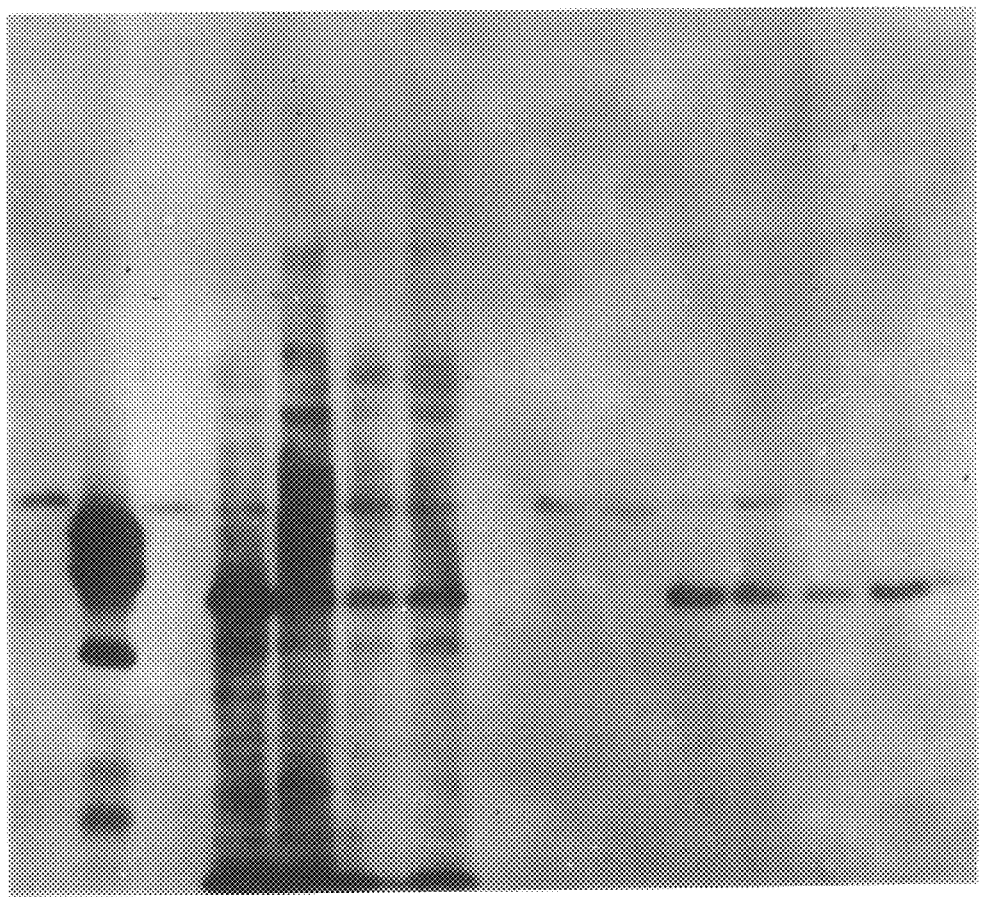
FIG. 3 shows a Western Blot of extracts from E. coli MM294 and of E. coli MC1000 lambda lysogen transformed with plasmids of the invention using controls of ricin A.

The leader sequences for the encoded proteins of FIGS. 12-1/12-2, 13-1/13-2, and 14-1/14-2 are the same.

MODES OF CARRYING OUT THE INVENTION

A. Definitions

As used herein, "ricin A" refers to a protein whose amino acid sequence is substantially similar to that of the ricin A peptide which is extractable from castor bean seeds. The ricin A of castor beans is approximately 265 amino acids in length and has a molecular weight of approximately 32,000 daltons. However, it is known that the precise sequence varies depending on the variety of bean, and, indeed that at least two slightly different forms of ricin A may be present in a single variety.

"Ricin B" refers to a protein whose amino acid sequence is substantially similar to that of the ricin B peptide which is extractable from castor bean seeds. The ricin B of castor beans is approximately 260 amino acids in length and has a molecular weight of approximately 34,700 daltons; as with ricin A, it is known that the precise sequence varies depending on the variety of bean.

"Substantially similar" means that the protein in question must be approximately the same length (arbitrarily within around 10% although it is known that the essential features for activity may reside in a peptide of shorter length—i.e., a "fragment", or of longer sequence—i.e., a fusion protein) but, more importantly, and critical to the definition, must retain the capacity of ricin A chain to interact with, and incapacitate, the 60S ribosome subunit. Alterations in chain length which do not greatly impair this enzymatic activity are included. It is well known that some small alterations in protein sequence may be possible without disturbing the functional abilities of the protein molecule, although other modifications are totally destructive. It is not currently possible to predict with any assurance into which category a particular alteration will fall. The definition herein permits any modifications which are in the first category. Such alterations could result from chance mutations in the gene, sequence or from deliberate alterations thereof. In summary, modified forms of acid sequence which retain the "enzymatic activity" of ricin A (see below) are included.

Further, as is well known, protein sequences may be modified by post-translational processing such as association with other molecules, for example, glycosides, lipids, or such inorganic ions as phosphate. The ionization status will also vary depending on the pH of the medium or the pH at which crystallization or precipitation of the isolated form occurs. Further, the presence of air may cause oxidation of labile groups, such as —SH. Included within the definition of ricin A are all such modifications of a particular primary structure—i.e., e.g., both glycosylated and non-glycosylated forms, neutral forms, acidic and basic salts, lipid or other associated peptide forms, side chain alterations due to oxidation or derivatization, and any other such modifications of an amino acid sequence which would be encoded by the same genetic codon sequence.

"Impurities" as used in describing ricin A or ricin prepared by the method of the invention refers to materials normally associated with these proteins as produced in the castor bean seeds, which are not included among the protein modifications above. Accordingly, "impurities" refers to agglutinin as well as to other castor bean cellular materials which ordinarily are associated with ricin or ricin A nonspecifically; with respect to ricin A per se, "impurities" includes ricin B.

As used herein, "soluble" refers to a protein which remains in the supernatant after centrifugation for 30 min at 100,000× g in aqueous buffer under physiologically isotonic conditions, for example, 0.14 M sodium chloride or sucrose, at a protein concentration of as much as 10 mg/ml. These conditions specifically relate to the absence of detergents or other denaturants in effective concentrations such as guanidine or urea.

"Ricin" refers to proteins having cytotoxic activity which contain both A and B chains, as set forth herein. Conventionally, as described above, ricin is distinguished from RCA in the art. Both ricin D and ricin E contain A and B chains; it appears that the differences in these proteins lies in the B portions.

"Precursor protein", for both ricin and RCA refers to the single chain protein which contains a "linker" peptide between the A and B portions. The linker, in the native form is a dodecamer. The linker associated with the specific ricins herein has the same sequence in all three ricin related clones obtained. This native sequence may be conveniently modified to provide, for example, a trypsin cleavage site. Such modified proteins are also "precursor protein". In addition, DNA encoding the precursor protein may be modified so that stop and start translation codons are present within the sequence between the A and B portions. This construction results in the production of separate A and B proteins, but the construct is nevertheless herein defined to encode a "precursor protein". The stop and start codons may be located at any convenient positions within the linker sequence; ie, the resultant A or B portion may contain some additional sequence.

"Biologically active" refers to retaining the enzymatic or other biological behavior which typifies the function of the protein in its native state. The biological activity of ricin A refers in one aspect to enzymatic activity, i.e., its ability to inhibit protein synthesis in a rabbit reticulocyte in vitro translation system (a commercially available system obtainable, e.g., from Bethesda Research Laboratories, Rockville, Md.). In addition to being enzymatically active, soluble preparations of ricin A toxin are also capable of exhibiting specific cytotoxic activity when conjugated with specific binding portions, for example, immunoglobulins, to form immunotoxins.

"Cytotoxic activity" refers to the specific ability of these immunotoxins to cause the destruction of cells against which they are targeted, as opposed to being generally toxic to an organism. Cytotoxic activity may be demonstrated both in vitro using cell cultures comprising the target cells or in vivo using implants or naturally occurring groups of targeted cell types. In summary, the biological activity of ricin A may be demonstrated in accordance with at least three criteria: enzymatic activity in inhibiting protein synthesis, in vitro cytotoxic activity when cultured cells containing antigens specific to an immunoglobulin binding entity conjugated to the toxin are selectively killed by these immunoconjugates, and in vivo cytotoxicity wherein immunotoxins are capable of binding to and selectively killing cells reactive with the antibody which forms the binding moiety in the immunoconjugate. It is recognized that some or all of these biological activities may be absent even when immunological cross reactivity with antibodies raised against the specified protein remains.

"Secretion" refers to transport through the cellular membrane. Whether or not the protein appears in the medium is dependent on the presence or absence of a cell wall; in the presence of cell walls the secreted protein will be found in the periplasm, in the absence of cell walls it will be in the medium.

"Alkaline phosphatase A" (phoA) refers to the alkaline phosphatase structural gene of *E. coli* K12 as, for example, disclosed by Kikuchi, Y., et al, *Nucleic Acids Res* (1981) 9:5671–5678. The structural gene is located at 8.5 minutes on the *E. coli* genetic map (Bachmann, B. J., et al, *Microbiol Rev* (1980) 44:1–56) and its native expression is relatively complex. However, the promoter and N-terminal regions have been sequenced (Kikuchi, Y., et al, (supra)) and the sequence of the signal peptide deduced (Inouye, H., et al, *J Bacteriol* (1982) 149:434–439). The definition herein encompasses not only the specific structural gene and portions thereof, but functional equivalents derived from other bacterial sources or synthesized in vitro. It is understood that minor modifications may be made in the nucleotide sequences without affecting functionality, and that sequences derived from different strains or species of procaryotic cells may, and indeed almost surely do, contain sequences not absolutely identical to that of the abovementioned source. In addition, in connection with the invention herein, modifications have been made to this sequence to provide suitable restriction cleavage sites, wherein these modifications do not result in loss of functionality.

Figure 5A:
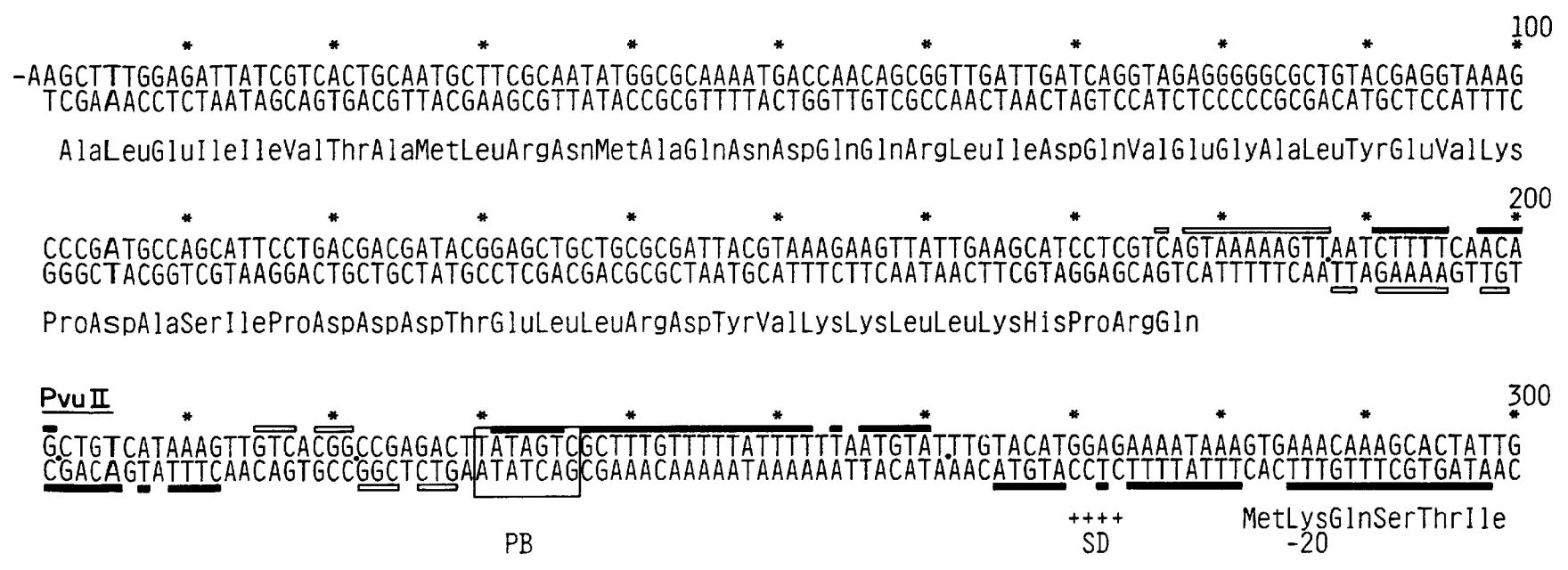
Figure 5B:
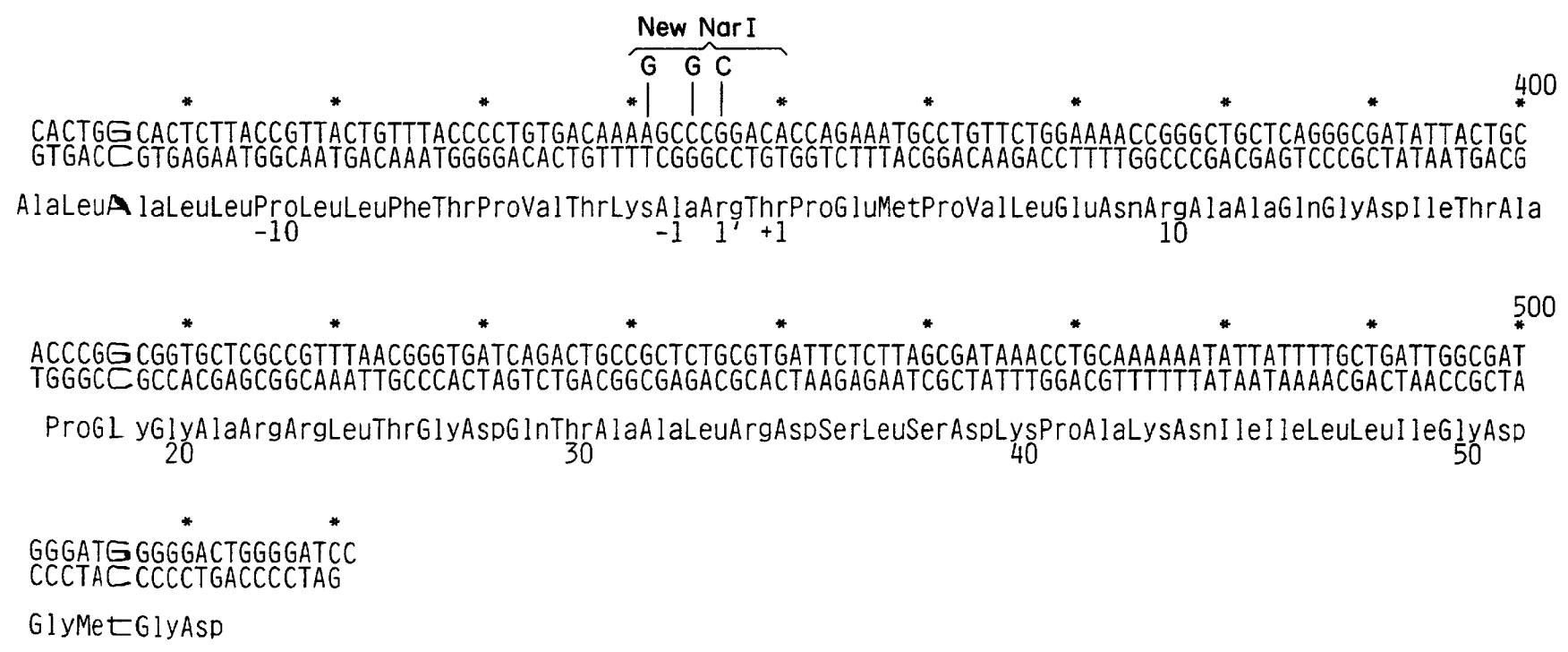

Of relevance to the present invention are the following regions of the alkaline phosphatase structural gene: the promoter, the ribosome binding site, the leader sequence, and the positive retroregulator sequence. The upstream controls and leader are used in the illustration below; the positive retroregulator region is substituted by the corresponding region of the B. thuringiensis crystal protein gene. The nucleotide sequence of the 520 bp fragment which includes the promoter, ribosome binding site, and signal are disclosed in Kikuchi, Y., (supra). The nucleotide sequence of the leader, modified to provide a NarI site is shown in FIGS. 5A and 5B. This modification permits coding sequences other than alkaline phosphatase to be substituted in reading frame with leader, and in that sense the leader is still functional. However, conversion to the NarI site prevents processing with respect to alkaline phosphatase itself since the codon for the N-terminal arginine of the alkaline phosphatase sequence is now converted to a proline. Functionality with respect to inserted sequences is not impaired as this portion of the NarI site is eliminated in the junctions.

A "terminated" leader sequence refers to a leader peptide encoding DNA having a stop codon in reading frame proximal to its normal carboxy terminus. In the expression systems of the invention, the termination codon is also proximal to the ATG start codon of the desired heterologous protein to be expressed. Accordingly, the leader or the desired "mature" protein may have slightly fewer or slightly more amino acids encoded in this junction region than their native counterparts.

"Operably linked" when used in describing DNA sequences refers to juxtaposition in such a way that the functionality of the sequences is preserved. Thus, for example a coding sequence "operably linked" to control sequences is positioned so that the these sequences are capable of effecting the expression of the coding sequence.

"Control" sequence refers to those DNA sequences which control initiation and termination of transcription and translation. In procaryotic systems, for example, control sequences, comprise promoter or promoter/operator and nucleotides encoding a ribosome binding site; in eucaryotes, promoters, terminators and enhancers appear to be involved.

"Recombinant host cells" refers to cells which have been transformed with DNA sequences constructed by recombinant techniques. Such reference includes both the cells as separated, for example by filtration or as a centrifugation pellet, and to cultures of these cells. Indeed, "cells" and "cell cultures," where the context so permits, are used interchangeably herein. Also included in particular references to "cells" are the progeny thereof. Such progeny are either of the same genomic structure, or Contain a modified genome due to inherent instability, intentional mutation, or chance alterations in the genomic structure.

Cellular materials "associated" with ricin A are insoluble fragments which may be non-specifically bound to recombinant ricin A, such that the ricin A appears to be spun down when the debris is removed, even though when freed from this association, the ricin A may be soluble by the definition set forth above.

B. General Description

The approach followed to obtain recombinant ricin A is, briefly, as follows:

Retrieval of the Ricin A Coding Sequence

1. A CDNA library was constructed by isolating mRNA from maturing castor bean seeds, and preparing the corresponding cDNA by, in general, conventional methods. The oligonucleotide 5'-GACCATTTCGACCTACG-3' which complements the mRNA encoding the N-terminal region of the B chain (which is thus just downstream from the A chain codons) was used as primer in synthesizing the single stranded copy; and an oligo dC homopolymeric tail was added to the 3' end to permit oligo dG to be used as primer in double stranding. The resulting double stranded CDNA fragments were then inserted into the PstI site of the cloning vector, pBR322, by annealing homopolymeric oligo dC tails provided by standard tailing methods to the cDNA with the oligo dG tails which are also thus provided on the cleaved vector. The ligation mixture is transformed into E. coli. About 5000 successful transformants were screened for hybridization with probe.

2. The oligonucleotide mixture 5'-GCATCTTCTTG GTTGTCNGGATGAAAGAAATAGGC-3' (wherein N is A, T, G, or C) was used as a probe. This sequence was initially predicted based on the amino acid sequence described in the review by Olsnes (supra) and verified as described in ¶D.2 below.

3. Positive colonies were analyzed by restriction and showed two pattern types—one predicted to be found from ricin A, and the other presumed to be associated with agglutinin A, since it was significantly different from that obtained from ricin A. A colony was obtained which contained the entire sequence for ricin A, as confirmed by sequencing and comparison of the deduced amino acid sequence to that of native ricin A. Plasmid DNA isolated from this colony was designated pRA123, and given number CMCC 2108 in the assignee's culture collection. pRA123 was deposited with the ATCC on Aug. 14, 1984, and has accession no. 39799.

It should be noted that the procedures of the foregoing paragraphs need not now be repeated in order to obtain the desired ricin A encoding sequences. The full length nucleotide sequence encoding ricin A is shown in FIG. 1, and is deposited at ATCC. Using methods known in the art, the appropriate sequence spanning approximately 750 nucleotides may be synthesized. (See, for example, Edge, M. D., et al *Nature* (1981) 292:256; Nambiar, K. P., et al, *Science* (1984) 223:1299; or Jay, Ernest, et al, *J Biol Chem* (1984) 259:6311.) Desired sequence modifications useful in obtaining the desired portions of the ricin A sequence or appended sequences for the construction of expression vectors may be made, using site-specific mutagenesis in a manner analogous to that described for the construction of expression vectors below.

Construction of Expression Sequences for Ricin A and Vectors Containing Them

4. The cDNA insert in pRA123, which contained the coding sequence for the entire ricin A chain, was modified by primer directed mutagenesis to place a HindIII site in front of a newly constructed ATG start codon preceding the RTA sequence, and to place a stop signal at the C-terminus.

5. The properly terminating coding sequence for the ricin A chain could then be removed as a HindIII/BamHI cassette and ligated into appropriate expression vectors. Two host expression vector systems were used: pTRP3 which provides a trp promoter and ribosome binding site immediately preceeding the HindIII site, and pPLOP which contains the lamda $P_L$ promoter and the N gene ribosome binding site immediately upstream from the HindIII site, as well as a temperature controlled replicon.

6. Alternatively, expression sequences employ the phoA promoter/operator and leader sequence and suitable retroregulators. pSYC1089, containing the phoA upstream sequences and the positive retroregulator derived from *B. thuringiensis* crystal protein gene is conveniently used as source of the control sequences. The positive retroregulator is extensively described in U.S. Ser. No. 646,584, filed Aug. 31, 1984, assigned to the same assignee, and incorporated herein by reference. Construction of pSYC1089 is described below.

7. The expression vectors were then transformed into suitable hosts--expression vectors derived from pTRP3 or pSYC1089 into *E. coli* strain K12 MM294, and those derived from pPLOP into *E. coli* strain MC1000 lambda lysogen (see below). The transformed hosts were then cultured under suitable conditions for the production of the ricin A.

Production of Recombinant Protein

8. The heterologous protein produced by recombinant cells transformed with the resulting expression vectors pRAT1, pRAT7, pRAL6, pRAL7, pRAP218, pRAP2210 and pRAP229 was shown to be the desired ricin A by Western Blot, and by enzymatic activity of partially purified fractions.

In addition, ricin A protein produced by *E. coli* transformed with pRAP218, pRAP2210, or pRAP229 was in soluble form and associated with the intracellular environment. In addition to showing proper molecular weight and immunoreactivity by Western blot and enzymatic activity, the ricin A derived from pRAP229 transformants was shown to be cytotoxic both in vivo and in vitro.

9. Ricin A produced by pRAP229 transformants was purified to homogeneity using a series of chromatographic steps including treatment of a partially clarified sonicate with phenyl sepharose. The purified material was conjugated to antibodies reacting with transferrin or breast tumor cells to form immunotoxins, which immunotoxins were demonstrated to have the above-mentioned in vitro and in vivo cytotoxicity.

10. For expression of whole ricin, the cDNA insert of pRA123 is modified only in the region of the A chain start codon, and plasmids analogous to pRAL6 and pRAT1, but without the stop codon at the A chain C-terminus are thus obtained in a manner identical to that described in ¶5 above. The remaining codons to complete the ricin sequence are then inserted into these analogous plasmids.

11. Expression of secreted forms of ricin or ricin A may also be achieved in appropriate vector/host systems such as those of yeast, plant or mammalian cells, which are capable of correctly processing ricin precursor and signal sequences. To obtain secretion, pRA123 is modified by primer directed mutagenesis so as to provide a HindIII site upstream of the ATG start codon preceding the signal sequence rather than at the native N-terminus. A suitable primer is shown in FIG. 1. If ricin itself is to be expressed, this is the only modification made in pRA123; if ricin A is to be secreted, the modification which provides a stop codon as previously set forth is also made. These suitably modified pRA123 sequences are then used to construct expression plasmids in a manner analogous to that set forth in ¶5 but incorporating eucaryotic control sequences. For those plasmids designed to produce secreted ricin, the remaining B portion coding sequences are provided in reading frame to the analogs without stop codons.

Retrieval of Full-Length Ricin and RCA Encoding Clones

12. The full-length sequences encoding ricin D, putative ricin E, and RCA in precursor form were obtained, using the messenger RNA prepared as described above for ricin A, to obtain a cDNA library, and then probing the library to retrieve the desired cDNA inserts. The library was prepared using the method of Okayama and Berg (*Mol and Cell Biol* (1983) 3:280–289) and was probed using the same 35-mer used for ricin A-encoding sequences. Out of several thousand transformants with cloning vector, a number of positively hybridizing clones were obtained.

13. Positively hybridizing colonies were subjected to restriction analysis and showed restriction patterns corresponding to ricin D and to RCA, and a third type which corresponded to neither. The cDNA inserts from representative clones of each of the three types were sequenced. The results of the sequence information are shown in FIGS. 12-1/12-2, 13-1/13-2, and 14-1/14-2. FIGS. 12-1 and 12-2 represents the RCA encoding insert; FIGS. 13-1 and 13-2 the sequence for the insert encoding ricin toxin D. i.e., the sequence which corresponds to that of the B chain of ricin previously disclosed, and FIGS. 14-1 and 14-2 shows the nucleotide sequence for the insert encoding a precursor presumed to be that for ricin E—i.e., protein having the toxin portion corresponding to ricin A, but a B chain containing primary amino acid sequence differences from that of the ricin B previously obtained.

As stated for ricin A above, the procedures set forth herein to isolate the sequences need not be repeated, as synthetic methods are available so that the DNA sequences shown in the figures can be constructed using chemical and enzymatic means in vitro.

Construction of Expression Vectors for Ricin and RCA

14. The inserts described above can be placed into expression vectors in a manner analogous to that described for ricin A. For the straightforward expression of the coding sequences contained in the isolated inserts,. the inserts are subcloned into M13 vectors for site-directed mutagenesis to place an ATG start codon and a HindIII site at the beginning of the mature protein, in a manner analogous to that set forth for ricin A above, or to place a HindIII site immediately prior to the ATG of the leader sequence where appropriate. The mutagenized DNAs can be retrieved from the M13 vectors by cleaving with PstI, blunt-ending with Klenow, digestion with HindIII at the newly created site, and isolation of the appropriate length sequence. The isolated fragment is then ligated into HindIII/BamHI (blunt) digested pTRP3 or pPLOP for convenient procaryotic expression as described for ricin A above.

15. The coding sequences of the inserts can also be ligated into expression vectors containing the PhoA promoter/ operator and leader sequence and suitable retroregulators, such as pSYC1089 as described above for ricin A, and as set forth in more detail below.

16. The expression vectors are then transformed into suitable hosts in a manner analogous to that set forth for ricin A above, and the protein recovered from the culture supernatant or the lysed cells. The precursor protein synthesized may be cleaved to excise the intervening dodecamer by the post translational processing effected by the cell per se in some hosts, or may be excised in vitro using appropriate enzymes or cell extracts. Excision of the dodecamer sequence may not be necessary for activity.

Modified Precursor

17. To facilitate conversion of the precursors to either RCA or the ricin toxins, modifications may be made, in particular in the linker portion, to provide suitable means for detaching the A and B portions. A variety of strategies are possible. Two convenient ones are: 1) construction of a trypsin cleavage site by creating an "arg—arg" form of the linker wherein the proline following the arginine residue already present is replaced by another arginine; and 2) insertion of a stop and a start codon in the linker region so that the A and B regions are separately but simultaneously produced.

Soluble Recombinant Ricin A

When the coding sequence for ricin A is placed into direct reading frame with the DNA encoding leader sequence of phoA in order to form a putative fusion peptide, so that the leader sequence is the N-terminal portion of a leader/ricin A chimera, the ricin A seuqences so disposed are not secreted. However, these constructs result in soluble cytotoxic material, as do constructs under the control of the trp promoter when the DNA is expressed in E coli MM294. This is in contrast to the case for constructs with the ricin A sequences under control of the $P_L$ promoter in MC1000. where the resulting product is relatively insoluble.

Analogous expression vectors containing the precursor proteins contained in pRT3, pRT17, and pRT38 or their mutagenized forms may be constructed in a manner analogous to those set forth above for ricin A. The construction is exactly as for ricin A, except that the DNA sequences downstream from the ClaI site used in the construction are also included. Transforming host cells with these expression vectors results in solubilization of the precursor encoded. The arg—arg modified precursor can readily be cleaved with trypsin; the A and B portions of the precursors can be produced as separate proteins, as herein described.

In the phoA expression system, the essential component is the terminated phoA leader sequence upstream of, proximal to, and out of frame with the ricin A encoding sequence, wherein the ricin A encoding sequence is initiated by an ATG codon. The two coding sequences must be, of course, provided with a compatible bacterial promoter which can conveniently be the phoA promoter already associated with the leader, but can be any compatible procaryotic promoter/ribosome binding site system. Additionally, production is improved in the presence of a positive retroregulator sequence which again, can either be the phoA positive retroregulator or, more advantageously, the positive retroregulator sequences associated with the crystal protein of *B. thuringiensis,* which are described extensively in U.S. Ser. No. 646,584 (supra). This and the other expression systems of the invention are typically provided on bacterial transport vectors which include such standard elements as replicons and selectable markers. The nature of these accessory elements does not form part of the invention, but optimization of these additional elements is understood to be desirable.

The vectors are then used to transform suitable procaryotic hosts, which are grown under conditions suitable for the particular host chosen, most frequently under conditions whereby the promoter placed in control of the expression system is suppressed. The production of the ricin A is then induced by providing conditions which effect expression under control of the chosen promoter and the production permitted to proceed for sufficient time to effect a desired accumulation of product. The protein product is then isolated by disrupting the cells, for example, by sonication or by mechanical means such as a French press, and the cellular debris removed. The ricin A produced by the invention system is then further purified using standard techniques known in the art as applied to freely soluble proteins. However, the efficiency of the extraction and purification is enhanced by treating partially clarified extract with phenyl sepharose. Phenyl sepharose appears to encourage the dissociation of the ricin A from cellular material with which it may be non-specifically bound. The solubility of the ricin A in the sonicate (once separated from the membrane or other associated materials) is shown by its ability to remain in the supernatant when the sonicate is subjected to centrifugation at high speed, 100,000× g for 30 minutes, to spin down insoluble proteins.

The importance of remaining soluble is particularly important in the context of purification procedures and testing for specific cytotoxicity. One commonly used method to obtain solubilization of recombinant proteins is to take them up in the presence of a detergent, such as, for example, urea, guanidine hydrochloride, or SDS. The detergent in the solutions, however, interferes both with the purification processes and with biological activity tests. Removal of the detergent from the solubilizing medium in many instances, and in particular in the instance of ricin A, results in reprecipitation of the protein, thus making it incapable of efficient purification and also rendering immunoconjugates formed using this material inactive in cytotoxicity tests.

Details of, and procedures used in, the strategy described in this paragraph are set forth in the paragraphs below.

C. Procedures

C1. Purification of mRNA

The mRNA encoding ricin, ricin agglutinin, and ricin A, was prepared as described below. Briefly, the method of Belamy, A. R., et al, *Methods in Enzymology* (1968) XII, Part B:156–160, was used with some modifications. One such modification succeeds in removing oxidized phenolic compounds from the preparations, which constitute a problem in messenger RNA prepared from plant tissue sources. The other results in destruction of the association of mRNA with ribosomal RNA which would interfere with dT affinity column chromatography.

In order to eliminate oxidized phenolics, the preparation was treated with Sephadex G-100. The gel retains the oxidized phenolics and passes the mRNA in the void volume. (Both polyphenolic compounds and transfer RNA were retarded.)

To eliminate the ribosomal RNA complexing, the suspension of RNA emerging from the foregoing G-100 column was reacted with a denaturant prior to applying the preparation to a dT affinity column.

C.2. Vectors and Host Cells

The specific embodiments described hereinbelow set forth procedures for constructing vectors compatible with procaryotes, and for transformation of such vectors into these host cells. *E. coli* K12 strain, MM294 and a lambda lysogen of *E. coli* strain MC1000, are described in particular. However, other microbial strains may also be used, such as bacilli, for example *Bacillus subtilis,* various species of Pseudomonas, or other bacterial strains. In such procaryotic systems, plasmid vectors which contain replication and other control sequences derived from a species compatible with the host are used. For example, *E. coli* is typically transformed using derivatives of pBR322, a plasmid derived from an *E. coli* species by Bolivar, et al, *Gene* (1977) 2:95. pBR322 contains genes for ampicillin and tetracycline resistance, and thus provides markers which can be either retained or destroyed in constructing the desired vector. Commonly used procaryotic control sequences which are defined herein to include transcription initiation, optionally operator, and ribosome binding site sequences, include such commonly used promoters as the beta-lactamase (penicillinase) and lactose (lac) promoter systems (Chang, et al, *Nature* (1977) 198:1056) and the tryptophan (trp) promoter system (Goeddel, et al, *Nucleic Acids Res* (1980) 8:4057) and the lambda derived $P_L$ promoter and N-gene ribosome binding site (Shimatake, et al, *Nature* (1981) 292:128). However, any available promoter system compatible with procaryotes can be used.

Ricin A and ricin are toxic to eucaryotic cells, and thus procaryotic hosts are preferred. However, eucaryotic hosts may be used in some circumstances; indeed ricin is natively produced in eucaryotes. It may thus be appropriate to utilize eucaryotic hosts if, for example, the signal sequence is retained for the ricin A or ricin, thus permitting secretion before the toxicity is experienced by the cell.

In the alternative, certain eucaryotic environments may provide modified processing of the ricin or ricin A so as to protect the cell against their potential toxcicity. Such mechanisms are not at present established; however it may prove possible to suppress toxcicity by a proper folding, glycosylation, or other alterations to the tertiary and derivative structure of the subject protein.

If eucaryotes are employed, eucaryotic microbes, such as yeast, may be used. *Saccharomyces cerevisiae,* Baker's yeast, is most commonly used although a number of other strains are commonly available. A number of plasmid vectors suitable for yeast expression are also known (see, for example, Stinchcomb, et al, *Nature* (1979) 282:39, and Tschempe, et al, *Gene* (1980) 10:157). Promoters for yeast vectors include promoters for the synthesis of glycolytic enzymes (Hess, et al, *J Adv Enzyme Reg* (1968) 7:149; Holland, et al, *Biochemistry* (1978) 17:4900). Any vector containing a yeast compatible promoter, origin of replication and other control sequences is suitable.

Similarly, it has been found possible to express genes encoding polypeptides in eucaryotic host cell cultures derived from multicellular organisms. See, for example, *Tissue Cultures,* Academic Press, Cruz and Patterson, editors (1973). Useful host cell lines include VERO and HeLa cells, and Chinese hamster ovary (CHO) cells. Expression vectors for such cells ordinarily include promoters compatible with mammalian cells such as, for example, the commonly used early and late promoters from Simian Virus 40 (SV 40) (Fiers, et al, *Nature* (1978) 273:113).

Finally, cells from and portions of higher plants have been found useful as recombinant hosts, and appropriate control sequences are available for expression in these systems. A suitable promoter and polyadenylation signal are those of the nopaline synthase (NOS) gene derived from the 3.2 kilobase (kb) HindIII-23 DNA fragment in the T-DNA region of *A. tumefaciens* Ti plasmid pTiT37 (Bevan, M., et al, *Nucleic Acid Res* (1983) 11:369; Depicker, A., et al, *J Mol Appl Genet* (1982) 1:5613). Suitable plant cells include cells derived from, or seedlings of, tobacco, petunia, and cotton. Other promoters include the maize promoter for alcohol dehydrogenase-1 or alcohol dehydrogenase-2 (Gerlach, W. L., et al, *Proc Natl Acad Sci* (USA) (1982) 79:2981), cauliflower mosaic virus promoter (Daubert, S., et al, *Virology* (1982) 122:444), and wheat promoter associated with the small subunit of ribulose biphosphate carboxylase (Broglie, R., et al, *Biotechnology* (1983) 1:55). Other polyadenylation signals which are available presently include those found on any of the above genes, or those of Schuler, et al, (Schuler, M. S., et al, *Nucleic Acid Res* (1982) 10:8225).

For procaryotes or other cells which contain substantial cell wall barriers transformation is done using the calcium treatment employing calcium chloride, as described by Cohen, S. N., *Proc Natl Acad Sci* (USA) (1972) 69:2110. For mammalian cells without such cell walls, the calcium phosphate precipitation method of Graham and van der Eb, *Virology* (1978) 52:546 is preferred. For plant cells, direct transformation of protoplast preparations in the presence of polyethylene glycol is employed. Krens, et al, *Nature* (1982) 296:72.

The successful expression attained by the invention depends upon correct utilization of the suitable control sequences to regulate expression of the desired toxin fragment. Therefore, whatever the host, control sequences compatible with and suitable for that host are positioned operably with respect to the coding sequence, using a properly placed "start" codon at the 5' end of the desired sequence. Any "native" control sequences are eliminated. The vectors of the invention place the coding sequence for the ricin A or ricin peptide, immediately preceded by an ATG start codon directly downstream from control systems chosen to be compatible with the particular host.

It is also important, in obtaining good production of, the desired fragments, to regulate the "time" of production so as to minimize any lethal effect on the host cell. Most typically, even for procaryotes, this is done by delaying expression of the ricin or ricin A sequences until substantial growth has occurred. Accordingly, it is desirable to utilize control sequences which are subject to environmental conditions. By maintaining conditions that repress expression during growth phase, and then converting to conditions which permit expression at the desired time, the negative aspects of any potentially lethal effect can be minimized.

In a particularly preferred approach, these regulatable control sequences are compatible with procaryotic hosts. The trp promoter is a regulatable promoter where expression of the operably linked sequence can be controlled by the level of tryptophan in the medium. By maintaining high tryptophan levels during growth, expression is repressed. Depletion or competitive inhibition of tryptophan turns on the promoter and permits expression.

The $P_L$ promoter derived from lambda phage is regulatable, but the ricin A produced is insoluble. This promoter is regulated by a protein which can be temperature sensitive. (There are mutant forms of the wild type repressor, e.g., $CI_{857}$ which have this characteristic known in the art.) When used in a host which is able to synthesize this mutant form of repressor (such as *E. coli* K12 strain MC1000 lysogenic for the lambda phage $N_7N_{53}CI_{857}SusP_{80}$), the $P_L$ promoter will be switched on when the temperature is raised because the higher temperature inactivates the mutant CI repressor. Thus, the host cells can be grown at low temperature without, or with, low production of the foreign protein. The temperature is then raised when growth has been attained and ricin or ricin A production is desired.

When the phoA control sequences are employed, expression can be delayed by maintaining the cells in the presence of phosphate ion and then depleting the phosphate levels when expression is desired.

A plasmid which has temperature sensitive copy number control may also be applied. If the cells are grown at low temperatures, coding sequences contained in the plasmid are replicated at low levels; at higher temperatures, the number of such copies is increased. The amount of protein produced is thus indirectly managed by regulating the number of available copies or its coding sequence.

C.3. Methods Employed

Isolation of the mRNA fragments comprising the desired coding sequences is described in detail hereinbelow. The polyA RNA is used as a template to construct a CDNA library by means now well understood in the art. Several such methods are now available, details of which can be obtained by reference to Maniatis, E. F. et al, *Molecular Cloning*, Cold Spring Harbor Laboratory (1982); and Okayama, H. and Berg, P., *Mol Cell Biol* (1983) 3:280. The cDNA library is probed for the desired sequences using procedures after that of Grunstein and Hogness, *Proc Natl Acad Sci* (1975) 72:3961.

Vector construction employs ligation and restriction techniques known in the art. The quantity of DNA available can be increased by cloning the desired fragments, i.e., inserting into a suitable cloning vehicle, such as pBR322, pUC13 or pUC8, transforming and replicating in *E. coli,* and, optionally further enhancing through chloramphenicol amplification or by phage replication. The desired fragments can then be removed from the cloning vectors or phage and ligated to suitable promoters compatible with the host intended to be employed in the expression of the gene. Such hosts are then transformed with these expression vectors and cultured under conditions which favor stabilization of the plasmid and the safe production of the desired toxin fragments. Such conditions might include repression of, the controlling promoter until most of log phase growth has been completed, and then altering conditions so as to favor the synthesis of the peptide. If the peptide is secreted, it can be recovered from the medium. If not, or if secreted into the periplasmic space, the cells are lysed, and the desired fragment recovered from the lysate.

Construction of suitable vectors containing the desired coding and control sequences employs standard ligation and restriction techniques which are well understood in the art, isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 $\mu$g of plasmid or DNA sequence is cleaved by one unit of enzyme in about 20 $\mu$l of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform which may be followed by ether extraction and the nucleic acid recovered from aqueous fractions by precipitation with ethanol or by running over a Biogel P-6 spin column followed by lyophilization to concentrate the sample. If desired, size separation of the cleaved fragments may be performed by polyacrylamide gel electrophoresis using standard techniques. A general description of size separations is found in *Methods in Enzymology* (1980) 65:499–560.

Restriction cleaved fragments may be blunt ended by treating with the large fragment of *E. coli* DNA polymerase I (Klenow) in the presence of the four nucleotide triphosphates (dNTPs) using incubation times of about 15 to 25 min at 20 to 25° C. in 50 mM Tris pH 7.6, 50 mM NaCl, 6 mM $MgCl_2$, 6 mM DTT and 0.1 mM dNTPs. The Klenow fragment fills in at 5' sticky ends but chews back single strands, even though the four dNTPs are present, at 3' sticky ends. If desired, selective repair can be performed by supplying only one of the, or selected, dNTPs within the limitations dictated by the nature of the sticky ends. After treatment with Klenow, the mixture is extracted with phenol/chloroform and ethanol precipitated and/or followed by running over a Biogel P-6 spin column.

Treatment with S1 nuclease under appropriate conditions results in rapid hydrolysis of any single-stranded portion of DNA and slow hydrolysis of double-stranded portions commencing at the ends. S1 nuclease hydrolyses are typically conducted in a buffer which is 15 mM sodium acetate, pH 4.5, 300 mM NaCl, and 1 mM $ZnSO_4$, using approximately 200 units per $\mu$l of S1 nuclease; Ordinarily, 50–100 units of S1 nuclease is used to hydrolyze approximately 10 $\mu$g of DNA.

Exonuclease III attacks double-stranded DNA, but hydrolyzes beginning at the 3' end of the nucleotide sequence. Thus, digestion of a double-stranded DNA results in two 5' protruding sticky ends. Hydrolysis is carried out in a buffer containing 15 mM Tris, pH 8, 10 mM NaCl, 1 mM $MgCl_2$, and 0.1 mM DTT, using approximately 2000 units per $\mu$l exonuclease III. Ordinarily, 150 units of exonuclease III were used to react with 10 $\mu$g DNA.

Synthetic oligonucleotides are prepared by the triester method of Matteucci, et al (*J Am Chem Soc* (1981) 103:3185–3191). Kinasing of single strands prior to annealing or for labeling is achieved using an excess, e.g., approximately 10 units of polynucleotide kinase to 1 nmole substrate in the presence of 50 mM Tris, pH 7.6, 10 mM $mgCl_2$, 5 mM dithiothreitol, 1–2 mM ATP, 1.7 pmoles $^{32}$P ATP (2.9 mCi/mmole), 0.1 mM spermidine, 0.1 mm EDTA.

Ligations are formed using approximately equimolar amounts of the desired DNA fragments (2–10×excess of linkers or small oligomers) suitably end tailored to provide correct matching, by treatment with an excess, i.e., in a typical 15–30 $\mu$l reaction 0.4–4 Weiss units T4 DNA ligase and, when blunt-ended ligation is involved, 0.4–1 units of RNA ligase. Ligation mixtures are buffered at approximately pH 7.6 using 66 mM Tris along with 5 mM magnesium ion, 5 mM dithiothreitol, 1 mM ATP, and 0.1 mg/ml BSA for either blunt-end or sticky end ligations. Incubations are carried out at approximately 14 to 25° C. overnight.

In vector construction employing "vector fragments," the vector fragment is sometimes treated with bacterial alkaline phosphatase (BAP) in order to remove the 5' phosphate and prevent religation of the vector. BAP digestions are conducted at pH 8.3 in approximately 50 mM Tris, in the presence of $Na^+$ and $Mg^{+2}$ using about 1 unit of BAP per $\mu$g of vector at 600 for about one hour. In order to recover the nucleic acid fragments, the preparation is extracted with phenol/chloroform and ethanol precipitated and desalted by application to a Biogel P-6 spin column. Alternatively, religation can be prevented in vectors which have been double digested by additional restriction enzyme cleavage of the unwanted fragments.

Oligonucleotide induced mutagenesis is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, the resulting double-stranded DNA is transformed into a phage-supporting host bacterium, and the cultures are permitted to grow. Cultures are then spread on plates permitting further growth of colonies arising from single cells which harbor the phage.

Theoretically, 50% of the new colonies will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Colonies containing phage which hybridizes with probe are then picked, cultured, and the DNA recovered.

In more detail, approximately one pmole of the pnage single stranded DNA template is mixed with approximately 10 pmoles of the synthetic oligonucleotide primer in 15 μl of 10 mM Tris, 10 mM $MgCl_2$, 90 mM NaCl. The mixture is heated to 67° for 3–5 min and then to 42° for 30 min The mixture is then cooled on ice, and a cold solution containing the 4 dNTPs at 500 μM and 3–5 units of Polymerase I (Klenow) in sufficient buffer to bring the volume to 20–25 μl is added. The mixture is left at 0° C. for 5 min and then brought to 37° for 30 min. The Klenow is then inactivated for 15 min at 75°, and the mixture transformed into an appropriate host, such as *E. coli* JM103, *E. coli* JM105, or *E. coli* DG98 (ATCC #39768) using 1 μl reaction mixture per 300 μl cells, which are grown on yeast extract-typtone agar plates. The resulting phage plaques are transferred to filters by lifting onto nitrocellulose, and pre-hybridized in 5 ml/filter of 6× SSC, 5× Denhardt's, 0.1% SDS, 50 μg/ml carrier (yeast RNA salmon sperm DNA etc.) at the desired temperature for 1–2 hr.

The fixed, pre-hybridized filters are then hybridized with $2\times10^5$ cpm/ml of kinased synthetic primer oligonucleotide (approximately $2-10\times10^7$ cpm/μg) for 3–16 hr, and then washed in 6× SSC once at room temperature for 5 min and then at the appropriate stringent temperature for 5 min. A simultaneous control run containing the original phage is used to verify that hybridization does not take place to the non-mutagenized strands.

In the constructions set forth below, correct ligations for plasmid construction are confirmed by transforming *E. coli* strain MM294 obtained from *E. coli* Genetic Stock Center, CGSC #6135, or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci* (1969) 62:1159, following chloramphenicol amplification (Clewell, D. B., *J Bacteriol* (1972) 110:667) and analyzed by restriction and/or sequenced by the method of Messing, et al, *Nucleic Acids Res* (1981) 9:309, or by the method of Maxam, et al, *Methods in Enzymology* (1980) 65:499.

Transformations in the examples below were performed using the calcium chloride method described by Cohen, S. N., et al, *Proc Natl Acad Sci* (USA) (1972) 69:2110.

Two host strains were used in cloning and expression of the plasmids set forth below:

For cloning and sequencing, in particular, *E. coli* strain MM294 (supra), Talmadge, K., et al, *Gene* (1980) 12:235; Meselson, M., et al, *Nature* (1968) 217:1110, was used as the host. However, when expression is under control of the $P_L$ promoter and $N_{RBS}$ the *E. coli* strain MC1000 Lambda $N_7N_{53}CI_{857}SusP_{80}$ as an expression host was used (ATCC 39531 deposited Dec. 21, 1983. This strain is hereinafter sometimes referred to as MC1000-39531). This strain contains a lambda prophage which codes for a temperature sensitive $C_I$ repressor, which at the permissive temperature (30–32° C.) is active. However, at the non-permissive temperature (36–48° C.), the repressor is inactive and transcription from the $P_L$ promoter can proceed. It is further characteristic of this strain that at elevated temperatures the prophage fails to induce.

The following examples illustrate the invention by describing the production of expression vectors suitable for production of ricin A fragment and of ricin in procaryotes. However, the ricin peptides of the invention can be ligated into a variety of vectors suitable for a range of other hosts; subject to the restraint that in eucaryotes toxicity must be mitigated by protection or secretion.

D. Example

D.1. Isolation of Messenger RNA

Fifty g of immature castor beans (*Ricinus communis*) were placed in 100 ml homogenizing buffer (150 mM NaCl, 50 mM Tris, pH 8.3, 5 mM EDTA and 50 mM freshly added β-mercaptoethanol) to which was added 12 ml 0.2 M vanadium-ribonucleoside complex*, 30 mg proteinase K, and 15 ml 20% SDS. The mixture was homogenized by blending at high speed for 3–4 min in a Waring blender and then incubating 2–3 hr at room temperature with occasional blending.

*The vanadium ribonucleoside solution is prepared as follows: 893 mg $VOSO_4 \cdot 3H_2O$ was added to 2 ml water and the mixture boiled to dissolve the vanadium salt. A solution containing the 4 ribonucleosides was prepared by dissolving 1 mmole each of adenosine, cytidine, guanosine, and uridine in 17 ml water. Heat is required. 1 ml of the foregoing $VOSO_4$ solution was then added to the ribonucleoside solution and the resultant titrated to pH 6.5 with 10 N NaOH, and finally to pH 7 with 1 N NaOH while stirring in a boiling water bath. Formation of the complex is indicated by a change in color from bright blue to green-black. The solution was finally diluted to 20 ml with water.

The suspension was centrifuged for 15 min at 8000× g at 5° C. and the pellet discarded. The supernatant was strained through cheesecloth to remove lipids and the filtrate extracted sufficiently with phenol:$CHCl_3$:isoamyl alcohol, 24:24:1 containing 1% hydroxy-quinoline, to remove vanadium salts and protein, and the aqueous layer brought to 0.4 M with NaCl and 10 mM with EDTA. 2.5×volume absolute ethanol was added to precipitate nucleic acids, and the mixture stored at −20° C. overnight.

The precipitate was centrifuged for 15 min at 7000× g at 2° C., and the pellet resuspended in 9.5 ml aqueous solution 0.025 M NaCl, 0.025 M Tris, pH 8, plus 9.5 ml phosphate buffer (2.5 M total phosphate, $K_2HPO_4$:33% $H_3PO_4$, 20:1), plus 9.5 ml 2-methoxyethanol. The mixture was shaken and chilled on ice for 3–5 min with occasional mixing, and then centrifuged at 2000× g for 5 min at 2° C. The upper layer was removed and to this was added 10 ml 0.2 M sodium acetate, and 5 ml 1% cetyl trimethylammonium bromide (CTAB) and the mixture chilled on ice for 10 min. The resulting white precipitate was harvested by centrifugation at 2000× g for 10 min at 2° C. The precipitate was washed by addition of 70% ethanol containing 0.1 M sodium acetate and by re-centrifuging at 2500× g for 10 min at 4° C.

After removal of the supernatant, the pellet was resuspended in 2 ml G-100 column starting buffer (20 mM Tris, pH 8, 1 mM EDTA, 0.5% SDS), and then adjusted to contain 0.5 M NaCl. Solids were removed by centrifugation at 2000× g for 5 min at room temperature and the supernatant applied to a Sephadex G-100 column (1.5 cm×40 cm) and the column eluted using buffer similar to that applied to the column but lacking SDS. The eluate was assayed by monitoring $OD_{260}$. Desired messenger RNA was obtained in the flow through volume, leaving behind oxidized phenolic compounds present in the plant extract. (These compounds are known to behave similarly to polyA RNA on dT columns, inhibit protein synthesis, and thus interfere with the assay for mRNA.

The initial peak containing mRNA was treated with formamide, a denaturant, to destroy ribosomal RNA complexing. To do this, the mRNA containing fractions were pooled, precipitated in ethanol, and the precipitates redissolved in a minimum volume of water. To this solution was added 9 volumes of deionized formamide containing 20 mM PIPES (piperazine-N,N-bis(2-ethanesulfonic acid), pH 6.5–7.0.

The mixture was then warmed to 37° C. for 5 min, and 10 volumes of dT column buffer (0.5 M NaCl, 10 mM Tris, pH 7.5, 1 mM EDTA) added. The presence of formamide dissociates the polyA RNA from any ribosomal RNA present.

The denatured mixture was then run over an oligo dT column according to procedures well established in the art, and approximately 100 μg polyA RNA recovered upon elution.

D.2. Preparation of Ricin A and Full Length DNAs of Ricin and RCA

D.2.a. Ricin A

To obtain a ricin A-encoding clone, the poly A mRNA prepared as in the preceding paragraph is used to obtain a cDNA library according to the method of Maniatis, et al (supra). Briefly, a portion of the polyA RNA is treated under appropriate buffer conditions with reverse transcriptase in the presence of the primer $5^1$-GACCATTTCGACCTACG-3' which complements the mRNA encoding the N-terminal region of the B chain—i.e. is just downstream from the A chain codons. The complex is then treated with base to destroy the remaining mRNA. A poly dC oligomer is added to the 3' end of the single strand using terminal transferase under standard conditions. The resulting single-stranded cDNA is converted to the double stranded form using oligo-dG as primer, employing reverse transcriptase. The double stranded cDNA is then inserted into the PstI site of pBR322 by tailing the CDNA with oligo-dC and the cleaved vector with oligo-dG, and annealing The resulting mixture was used to transform *E. coli* MM294, and 5000 AmpR strains obtained.

Successful colonies were transferred onto nitrocellulose plates, and probed using the procedure of Grunstein & Hogness (supra), with the mixture of four synthetic oligonucleotides:

```
                         A
                         T
5'-GCATCTTCTTGGTTGTCCGGATGAAAGAAATAGGC-3'
                         G
``` which are kinased with $^{32}$P. This mixture represents the anti-sense strand complementary to the codons for the amino acid sequence contained in ricin A with most codon ambiguities resolved by sequencing cDNA synthesized using a mixture of primers to a portion of the codon sequence and employing the experimentally determined sequence of the synthesized cDNA. Plasmids were isolated from several representative positively hybridizing colonies, and analyzed by restriction analysis Two groups thus obtained appeared to correspond to ricin A and to agglutinin A. Two plasmids, one from each group, pRA123 and pRA45 were sequenced in the insert region FIGS. 1 and 2 show the results of this sequencing. FIG. 1 shows the sequence of the insert in pRA123. The base sequence permits the deduction of an amino acid sequence presented immediately below the nucleotide sequence in the figure. It can be compared to that of isolated protein, labeled RTA in the figure, only six residues differ. These difference may be due to errors in the published sequence and/or to varietal differences in the ricin A proteins represented. The entire coding sequence for ricin A is present, as well as codons for the 12 amino acids joining the A to B chain, and for the signal sequence. pRA123 was used as the source of the the coding sequence in the expression vectors described below after modification to provide correct start and stop codons.

FIG. 2 shows the sequence deduced for ricin agglutinin A from a combination of sequences in pRTA115 (see FIG. 4) and of pRA45. In that figure, the base sequence for this composite is shown, and the line immediately below it represents the deduced amino acid sequence. To show the differences from ricin toxin A, that sequence, labeled RTA is also included in the figure. The cysteine residues at positions 84 and 156 in the agglutinin sequence represent major differences from the toxin sequences obtained.

D.2.b. Full Length Ricin and RCA Clones

To obtain clones which encode the entire polypeptide sequences of ricin and RCA, the polyA mRNA prepared as in the preceding paragraph is used to obtain a cDNA library according to the method of Okayama and Berg (supra), using the vectors described therein. This method differs from that of Maniatis et al in that: (1) the plasmid vector DNA functions as the primer for the synthesis of the first cDNA strand; and (2) the second DNA strand is formed by nick-translation repair of the cDNA:mRNA hybrid. Briefly, the plasmid pcDV1 is used as primer DNA by adding an oligo dT tail to the KpnI generated terminus which is farthest from the HindIII site. The initial strand of cDNA is generated by incubating the primer with an excess of polyA mRNA and reverse transcriptase under the appropriate buffer conditions. After isolation of the plasmid-cDNA:mRNA hybrids, a dC tail is added to the 3' end of the cDNA. This is accomplished by incubating the vector hybrid with dCTP in the presence of terminal deoxynucleotidyl transferase, and subsequently cleaving it with HindIII to release a fragment of pcDV1 DNA which also contains an oligo-dC tail. The resulting hybrid vector contains a partial HindIII site. The plasmid is cyclized by annealing it with a linker derived from the plasmid pL1 which contains an oligo-dG tail opposite a partial HindIII site, and ligating it with *E. coli* DNA ligase. Subsequently, the second strand of cDNA, which replaces the RNA, is generated when the hybrid vector is incubated in a mixture which contains *E. coli* DNA ligase, *E. coli* DNA polI, and *E. coli* RNase H under temperature conditions which are optimal for repair synthesis and nick translation by polI (i.e. successive incubation at 12° C. and room temperature, for one hour each). The reconstructed vector contains the following significant features: (1) from pBR 322, the origin of DNA replication, and two genes for ampicillin resistance, and (2) from $SV_{40}$, the origin of DNA replication, the early and late promoters, the 16s RNA splice junctions: and the polyA addition signals. This vector is used to transform $$\frac{E.\ coli}{R}$$

MM294. Using this procedure several thousand $Amp^R$ colonies were obtained.

Colonies containing $Amp^R$ plasmids are probed by the procedure of Grunstein & Hogness (supra) using as probes the mixture of synthetic oligonucleotides discussed under ¶D.2.a.(above). Plasmids are isolated from several representative positively hybridizing colonies, and analyzed by restriction analysis. Based upon the restriction analysis patterns, three plasmids were selected for sequencing of the insert region; these were derived from clones pRT3, pRT17, and pRT38. These sequences are shown in FIGS. 12-1/12-2, 13-1/13-2 and 14-1/14-2.

FIGS. 12-1 and 12-2 shows the sequence of the insert in pRT3. The base sequence permits the deduction of the amino acid sequence presented immediately below the nucleotide sequence in the figure. A comparison of the amino acid sequence with that of the B chain of RCA presented in patent application Ser. No. 518,121 (supra), identified polypeptide encoded as RCA. The nucleotide sequence encodes the entire A and B chains and the twelve intervening amino acids, as well as a portion of the leader sequence.

FIGS. 13-1 and 13-2 shows the sequence of the insert in pRT17 and its deduced amino acid sequence. Based upon the amino acid sequence it is concluded that the nucleotide sequence encodes the entire A and B chains, the twelve intervening amino acids, and a portion of the leader sequence of ricin isotoxin D.

FIGS. 14-1 and 14-2 shows the sequence of the insert in pRT38 and the amino acid sequence deduced from it. From a comparison of the amino acid sequences encoded in pRT17 and pRT38, as presented in FIG. 15, it can be determined that the polypeptide encoded in pRT38 contains 15 amino acid substitutions relative to pRT17. All of the substitutions occur in the B chain. Thus, pRT38 encodes the entire A and B chains, the 12 intervening amino acids, and a portion of the leader sequence of a ricin isotoxin. Based upon the nature of the substitutions, from which it would be predicted that the pI of the B chain would be increased, the polypeptide encoded in pRT38 is tentatively identified as the ricin isotoxin, E.

D.3. Modification of Cloning Vectors pRA123 which contains the entire ricin A coding sequence was modified so that this sequence would be obtainable as a HindIII/BamHI cassette with a termination codon in the proper position after amino acid 265, and a start codon in the position immediately preceding the mature sequence. pRA123 was digested with BamHI, and the approximately 896 bp fragment isolated and subcloned into M13mp18 in an anti-sense orientation relative to the lac promoter in the m13 vector. The phage single stranded DNA was subjected to primer directed mutagenesis using the sequences shown as superscripts 2 & 3 in FIG. 1 as primers. The oligonucleotide shown near the beginning of the A chain sequence (2) imparts modifications insert an ATG start codon immediately preceding the A toxin N-terminal amino acid and a HindIII site in turn, immediately upstream of the ATG. The primer placed near the C-terminal end of the toxin coding sequence (3) replaces the serine codon with a TAA termination codon. The resulting modified phage were identified after each mutagenesis using the appropriate above primers as probes. The desired constructs were double digested with HindIII and BamHI and the appropriate ricin A encoding fragments isolated.

If vectors are to be prepared for expression of the complete ricin sequence using this vector, the mutation directed by primer 3 which alters the serine residue to a termination codon is omitted. If secretion of either ricin A or ricin is desired, the mutation directed by primer 2 is omitted, and that directed by primer labeled 1 in FIG. 1, in the region of the start codon for the signal sequence is substituted. This modification results in provision of a HindIII site immediately preceding the ATG codon of the signal sequence. Thus, in addition to the above described modifications which enable construction of vectors for ricin A production intracellularly, sequences can be provided for construction of vectors which result in secretion of ricin A, or of intracellular production or secretion of the entire ricin sequence. The vectors designed for secretion must, of course, be constructed for expression in appropriate hosts, as set forth above.

In a somewhat analogous manner, the inserts from pRT3, pRT17, and pRT38 are modified to obtain desired cassettes containing the coding sequences for insertion into expression vectors. Using the primer described above as primer 2 in FIG. 1, an ATG start codon immediately preceding the precursor N-terminal amino acid and an immediately upstream HindIII site can be placed into all three precursor containing coding inserts. However, since the B portions of the precursor DNAs contain several BamHI sites, a BamHI site as used for ricin A is impractical, and other provisions are therefore made. Briefly, pRT3. pRT17, and pRT38 are digested with XhoI, blunt ended with Klenow and the fragments are ligated into M13mp19 at the SmaI site. The M13 contained inserts are analyzed by restriction analysis for orientation relative to the lacZ reading frame, and those containing the anti-sense orientation are chosen. This orientation provides a PstI site in the linker region of the phage vector for convenient excission of the modified inserts. The phage vectors containing inserts in this orientation are subjected to site-specific mutagenesis, as described above using, primer 2, to obtain the desired modified insert. The modified recombinant forms of the phage vectors are then digested with PstI, blunt ended with Klenow, and then with HindIII. The fragment containing the correct length segment of DNA is isolated for ligation into expression vectors. These vectors, when transformed into procaryotes, result in expression of the three precursor forms encoded.

In order to facilitate conversion of the ricin or RCA precursor into ricin or RCA, it may be desirable to provide a site for proteolytic cleavage in the dodecameric linking amino acid sequence between the A and B portions of the precursor protein. One convenient approach is to replace the proline residue downstream of the arginine in the linker with another arginine residue, thus providing a site for cleavage with trypsin. This is accomplished by performing an additional mutagenesis using primer 4 as shown in FIGS. 13-1 and 13-2 while the insert remains in the phage vector. The insert is again recovered by PstI (blunt)/HindIII cleavage. When cloned into expression vectors, the modified DNA can be expressed in suitable transformants to obtain a precursor susceptible to cleavage with trypsin to form an active form of ricin, which, nevertheless contains additional amino acid sequence attached to the A and B chains.

For certain other constructions, as described below, the M13-contained inserts need to be mutagenized with primer 4 only, thus providing the arg—arg for trypsin cleavage when vectors are constructed in an alternative manner as follows: Expression vectors for the precursors including the trypsin-cleavable forms thereof, comparable to those for ricin A, can also be obtained by using any expression vectors constructed for ricin A, and substituting the downstream portions containing the additional desired sequences in place of the terminated C-terminal portion of ricin A. This is accomplished by digesting the ricin A vectors with BamHI, blunting with Klenow, and then digesting with ClaI to obtain an opened vector lacking a portion of the C-terminal region of ricin A. A ClaI/XhoI (blunt) fragment from the insert in pRT3, pRT17, or pRT38 containing the portion of the precursor downstream from the ClaI site, or from the mutagenized insert in the corresponding M13 phage, is then ligated into the opened ricin A vector. As the ClaI site cuts into the ricin A portion of the chain, this permits substitution of the downstream portions harbored in these vectors in place of the remainder of the terminated A chain. These constructions yield expression vectors which are equivalent to those described as constructed by the HindIII modified insert above.

In still another approach to simplify production of ricin or ricin agglutinin from precursor DNA, the inserts into M13 are mutagenized using primer 5, as shown in FIGS. 14-1 and 14-2. This primer provides a termination codon for the A chain and ATG start codon for the B portion, while looping out the intervening amino acids. Construction of expression vectors for the two proteins separately is then accomplished in an analogous manner D.4. Construction of Expression Vectors for Ricin A and Precursors for Ricin and RCA The HindIII/BamHI fragment prepared in the previous paragraph for ricin A or the modified or unmodified HindIII/PstI (blunt) fragments from the precursor vector inserts are ligated into the host expression vectors pTRP3 and PPLOP digested with HindIII/BamHI. (The BamHI site is blunted for insertion of precursor sequence.) pTRP3 is on deposit with ATCC, accession no. 39946, and contains the trp promoter immediately preceding a unique HindIII site. PPLOP is on deposit with ATCC, accession no. 39947, and contains the $P_L$ promoter and N gene ribosome binding site immediately preceding a unique HindIII site, in a temperature sensitive high copy number plasmid.

Ligation products with pTRP3 are transformed into *E. coli* MM294 to $Amp^R$. Plasmids are isolated from selected colonies. Two of these plasmids pRAT7 and pRAT1 were shown to contain the entire RTA sequence. Plasmids containing the complete ricin variant sequences are designated pRTT3, pRTT17, and pRTT38.

Ligation products with pPLOP are transformed into *E. coli* MC1000 lambda lysogen, and plasmids isolated from two of the $Amp^R$ colonies were designated pRAL6 (ATCC 39833) and pRAL7. These were also shown to contain the complete RTA coding insert. Plasmids containing the ricin sequences are designated pRTL3, pRTL17 and pRTL38.

In a similar manner, plasmids designed to express secreted ricin A are constructed using the HindIII/BamHI fragments prepared as described above from pRA123 which had been subjected to primer directed mutagenesis using primers 1 and 3 in FIG. 1, and from pRT17 and pRT38 which have been similarly treated (pRT3 does not contain complete leader). These plasmids contain the coding sequence for ricin A or precursor protein along with the signal sequence in operable linkage to suitable eucaryotic control sequences. In an appropriate vector/host system, i.e., e.g., yeast, plant or mammalian cells, expression of the coding portions of these plasmids results in the secretion of ricin A, ricin or agglutinin precursor, rather than intracellular production and retention.

Similarly, plasmids pRABT and pRABL which express complete ricin chains, can be prepared from intermediates made by using the pRA123 sequences modified by mutagenesis with primer 2 only. Into these intermediates the coding sequences for the B portion of ricin is inserted. The intermediate plasmids in each case, obtained as described above, are treated with BamHI and SalI followed by BAP to obtain a vector fragment which will frame the B-portion coding region and a portion of the B-donor vector sequences. pRTB704 is used as the donor of the B-portion containing fragment. pRTB704 is described in detail in U.S. Ser. No. 578,121 (supra) and the pertinent description is set forth in ¶D.8 herein.

To obtain the "B" fragment, pRTB704 is digested with SalI, then partially with BamHI, and the fragments are separated, by agarose gel electrophoresis. The large fragment containing the B portion sequence from the BamHI site immediately 3' of the N-terminal amino acid, to the SalI site in the pUC vector fragment is thus isolated. This fragment is then ligated with the BAPed vector, and the ligation mixture transformed into *E. coli* and selected for $Amp^R$. Successful transformants are grown, plasmid DNA isolated, and used to transform the suitable corresponding host for expression of the complete ricin chain.

Thus, in summary, representative vectors applicable to procaryotic host expression include:

| Vector | pRA123 modified w/primer | expression vector for | promoter/ host |
|---|---|---|---|
| pRAT1 | 2,3 | intracellular ricin A | trp/MM294 |
| pRAL6 | 2,3 | intracellular ricin A | $P_L$/MC100 λ lysogen |
| pRABT* | 2 | intracellular ricin | trp/MM294 |
| pRABL* | 2 | intracellular ricin | $P_L$/MC100 λ lysogen |

*These represent vectors completed by a BamHI/SalI fragment insert from pRTB704.

*These represent vectors completed by a BamHI/SalI fragment insert from pRTB704.

All of the ricin A expression vectors can be converted to vectors for expression of the precursor proteins encoded by pRT3, pRT17 and pRT38 by exchange of a ClaI/XhoI (blunt) fragment from these vectors, or of a ClaI/PstI(blunt) fragment from the phage vectors containing linker modifications, for a shorter CalI/BamHI (blunt) fragment from the expression vectors.

D.5. Expression of Ricin A Encoding Sequences pRAL6, pRAL7, pRAT1 and pRAT7 were transformed into the appropriate strains of *E. coli* (MC1000-39531) for pRAL's or MM294 for RAT's) and the cells grown under standard culture conditions. Sonicated extracts were analyzed for protein production using Western blot.

Analysis of cloned protein products by Western blot analysis is generally referenced by Bittner, M., et al, *Ann Biochem* (1980) 102:459–471, and Erlich, H. A., et al, *Infect Immun* (1983) 41:683–690. Proteins separated in SDS-polyacrylamide gels are transferred electrophoretically using commercially available apparatus (e.g., from BioRad Corp. or Hoeffer Scientific) to a suitable membrane support such as nitrocellulose, CNBr-activated paper, or one of a variety of commercially available derivatized nylon membranes (e.g., Gene Screen, Dupont/New England Nuclear or Pall Biodyne A, Pall Corp.). Various methods for transfer and membrane reaction may be used and are supplied by the manufacturer of the apparatus and membranes. Specific cloned antigens are detected utilizing specific antisera, e.g., rabbit anti-ricin A sera, and a secondary detection system, for example, $^{125}I$ protein A (commercially available, New England Nuclear) or horseradish peroxidase conjugated anti-rabbit sera, developed appropriately to visualize the reactions.

FIG. 3 shows Western blots of cell extracts from suitable *E. coli* hosts transformed with pRAL6, pRAL7, pRAT1 and pRAT7. Immunoreactivity was obtained with antibodies raised against natural ricin A in rabbits. The mobility of the protein product noted as 'rec A' in the figure is consistent with that of a non-glycosylated form of ricin A relative to the mobilities of the native, glycosylated forms, denoted ricin Al and $A_2$ in the figure. No immunoreactivity, except for acceptable background, was noted in extracts from cells cultured under identical conditions which contained the vectors, PPLOP and pTRP3, plasmids which do not bear ricin sequences. Analysis of Coomassie Blue stained SDS-polyacrylamide gels and of radioautographs of parallel Western blots permits estimates of production levels. For the pRAT1 transformants the recombinant RTA represents approximately 0.5% of total cell protein. For the pRAL6 transformants, the RTA can be approximately 5% of total cell protein.

To obtain purified, active protein, cultures of the foregoing transformants were lysed by sonication and the insoluble material recovered. This material was treated with a chaotropic agent, 8 M urea containing 0.5% SDS, to solubilize it and disperse protein aggregates. The resulting suspension was centrifuged to pellet residual insolubles and the supernatant applied to a Sephacryl S-200 (Pharmacia Co.) column to fractionate the protein components. Fractions containing approximately 80% homogeneous ricin A protein were identified using polyacrylamide gel analysis and these fractions assayed for enzymatic activity associated with ricin A, i.e., the ability to inhibit protein synthesis in a rabbit reticulocyte in vitro translation system (a commercially available system obtainable, e.g., from Bethesda Research Laboratories, Rockville, Md.). The purified protein was biologically active in this assay.

Similarly, transformants using pRTT3, pRTT17, or pRTT38 into E. coli MM294 or pRTL3, pRTL17, or pRTL38 into E. coli MC100 results in intracellular production of ricin agglutinin or the ricin isotoxins. Transformants containing analogous vectors having modification of the linker region, when induced, produce trypsin-cleavable precursor or the activated protein.

D.6. Alternate Constructions Yielding Soluble Recombinant Ricin A

In addition to the foregoing vectors, vectors were constructed which yield the recombinant ricin A intracellularly in a form which is soluble in the sense defined above. In addition to being enzymatically active, the ricin A produced in this manner is active in the cytotoxicity assays described below. The following sections describe the construction of the vectors for such expressions the expression of the ricin A sequences, and the purification and characteristics of the ricin A protein produced. All of the vectors used in the construction use a host vector containing suitable control sequences derived from phoA and from B. thuringiensis.

Figure 6:
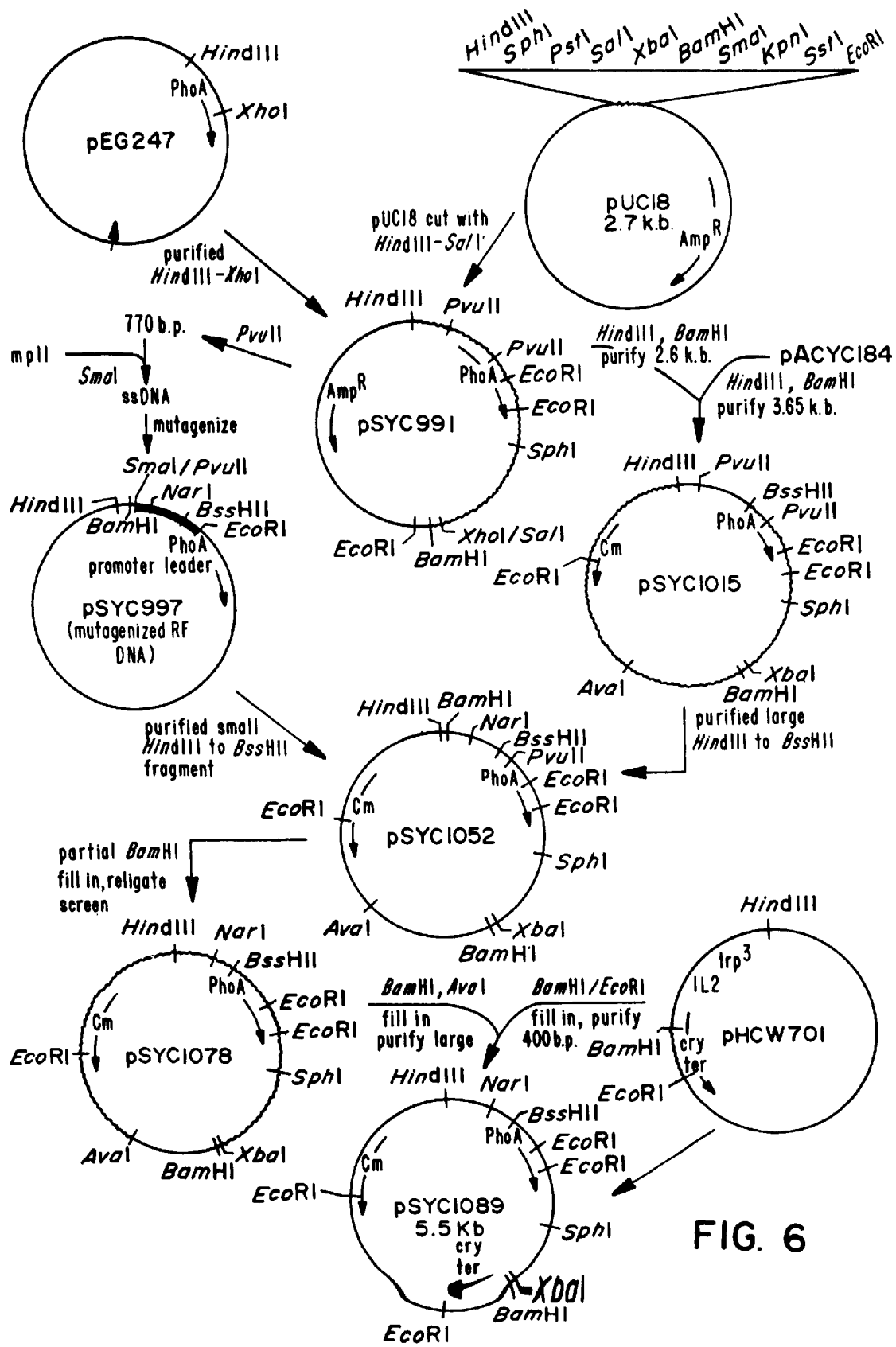
FIG. 6 shows the construction of pSYC1089, a host vector for expression of the proteins of the invention.

D.6.a. Construction of a Host Vector with Appropriate Control Sequences pSYC1089 contains the phoA promoter, leader and coding sequence with a modification to provide a NarI site at the C-terminal end of the leader sequence, followed by the B. thuringiensis positive retroregulator. The construction of this plasmid, which was used in further vector construction is shown in FIG. 6.

pSYC997: PhoA Promoter and Leader, Modified to Contain NarI Site

Plasmid pEG247, a 25 kb plasmid containing the 2.6 kb phoA structural gene as a HindIII/XhoI fragment was used as a source of the phoA gene. This plasmid was obtained from M. Casadaban and was constructed in a manner analogous to that set forth in Groisman, E. A., et al, *Proc Natl Acad Sci* (USA) (1984) 81:1840–1843. Indeed, by applying the procedures set forth in the foregoing reference, the phoa gene may be conveniently cloned into any desirable backbone vector.

The HindIII/XhoI 2.6 kb fragment from pEG247 was purified and cloned into pUC18, a 2.7 kb plasmid containing an ampicillin resistance marker and a polylinker permitting convenient insertion of desired sequences. pUC18 was digested with HindII/SalI, and the linear vector ligated with the isolated phoA fragment. The ligation mixture was used to transform E. coli DG99, a strain analogous to E. coli JM103 or JM105. to $Amp^R$, and the construction of the intermediate plasmid pSYC991 in successful transformants screened for inserts into pUC18 was verified.

pSYC997 which contains the desired NarI modification was prepared from pSYC991 by site-directed mutagenesis. The PvuII/PvuII 770 base pair fragment was obtained from pSYC991. It includes a portion of the phoA promoter and the upstream N-terminal sequences of the mature alkaline phosphatase, and thus, also, the entire leader sequence. This fragment was ligated into the SmaI site of M13mp11 and single stranded phage was prepared as template for the mutagenesis. In the mutagenesis, the synthetic 26-mer, 5'-TTCTGGTGTC$\overline{GGCGCC}$TTTGTCACAG-3'

(the superscript line shows the NarI site) was used as primer and probe. The mutagenized phage particles were then used to prepare RF-DNA as a source for the desired leader sequence containing the NarI site.

pSYC1015: $Cm^R$ Marker Backbone Vector pSYC1015, which provides chloramphenicol resistance, a replicon, and suitable restriction sites in the phoA gene, is also constructed from pSYC991. PSYC991 was first digested with HindIII/BamHI, and the approximately 2.6 kb fragment containing the phoA gene was purified and ligated with the purified 3.65 kb vector fragment from HindII/BamHI-digested pACYC184. pACYC184 is available from ATCC and contains the chloramphenicol gene ($Cm^R$), a bacterial replicon, and HindIII and BamHI sites in the tetracycline resistance gene. The ligation mixture was used to transform E. coli MM294 to $Cm^R$, and the construction of pSYC1015 was verified by restriction analysis and sequencing.

Additional phoA-Containing Intermediates

Two additional intermediate plasmids. pSYC1052 and pSYC1078, were constructed, as shown in FIG. 6, in order to provide a suitable host vector for the B. thuringiensis positive retroregulator.

pSYC1052 was constructed by ligating the purified small HindIII/BssHIII fragment containing the phoA promoter and NarI site from modified leader pSYC997 into HindIII/BssHIII-digested pSYC1015, which has, thus, the unmodified phoA sequences deleted. The resulting vector pSYC1052 was confirmed in E. coli transformants to $Cm^R$.

pSYC1078 is a modified form of pSYC1052 with the BamHI site in front of the phoA promoter deleted. In order to delete this BamHI site, pSYC1052 was subjected to partial BamHI digestion, filled in using DNA polymerase I (Klenow) in the presence of the four dNTPs, and religated under blunt-end conditions. The desired resulting plasmid, now containing a unique BamHI site just 3' of the phoA gene, was confirmed after screening successful $Cm^R$ transformants.

pHCW701: Source of the Retroregulator

The ability of the 3' sequences of the gene encoding crystal protein from B. thuringiensis (the cry gene) to enhance the expression of upstream coding sequences was described and claimed in copending U.S. patent application Ser. No. 646,584 (supra). Briefly, these sequences are characterized by a DNA sequence which transcribes to a corresponding RNA transcript capable of forming a stem and loop structure having a cytosine-guanine residue content of about 43%. When ligated about 30–300 nucleotides from the 3' end of the gene, a positive retroregulatory effect is shown on the gene expression. The positive retroregulator was prepared as a 400 bp EcoRI/BamHI restriction fragment, which was blunt ended and ligated into pLW1, an expression vector for interleukin-2. (pLW1 is a pRBR322 derivative containing a replicon effective in E. coli, a $Tet^R$ gene, the E. coli trp promoter, ribosome binding fragment and a 706 bp HindIII/PstI DNA fragment which includes the gene for human IL-2.

pLW1 has been deposited with ATCC under the terms of the Budapest Treaty and has accession no. 39405.)

Thus pHCW701 was completed by blunt ending the 400 bp EcoRI/BamHI fragment containing the positive retroregulator of the cry gene with Klenow and the four dNTPs, and ligating the blunt-ended fragment using T4 ligase and ATP into StuI-digested plasmid pLW1. Two possible orientations result; they can readily be distinguished by restriction analysis. The orientation with the regenerated BamHI site located nearer the 3' end of the IL-2 gene was designated pHCW701 and deposited with ATCC under the terms of the Budapest Treaty. It has accession no. 39757.

Completion of PSYC1089

To complete pSYC1089. pHCW701 was digested with EcoRI, filled in using Klenow and the four dNTPs, then digested with BamHI, and the 400 bp fragment containing the positive retroregulator recovered. pSYC1078 was digested with AvaI, filled in with Klenow and the four dNTPs, and then digested with BamHI. The ligation mixture was transformed into *E. coli* MM294 and the construction of the desired plasmid pSYC1089, a 55 kb plasmid conferring $Cm^R$, was confirmed. pSYC1089 contains the sequences for the phoA promoter and leader (with NarI site) sequence and structural gene immediately upstream of a BamHI site, followed by the positive retroregulator sequences of the cry gene.

D.6.b. Construction of Expression Vectors Using PSYC1089

The ricin A coding sequences were obtained from pRA123, more specifically, an M13 subclone of pRA123, described below, and pRAT1. pRA123 was deposited with ATCC Aug. 17, 1984 and has accession no. 39799.

Figure 7:
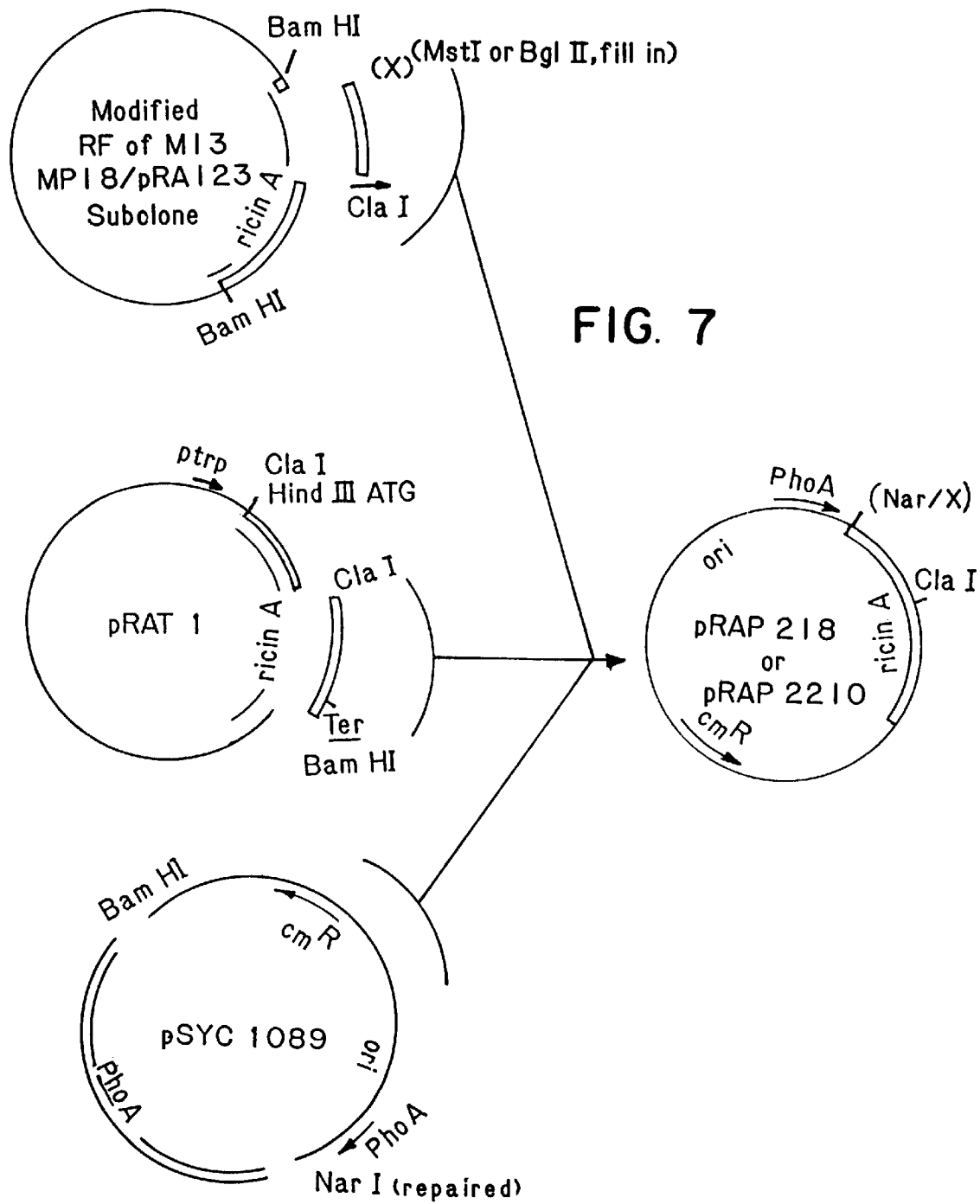
FIG. 7 shows the construction of pRAP2210 and pRAP218.
Figure 8:
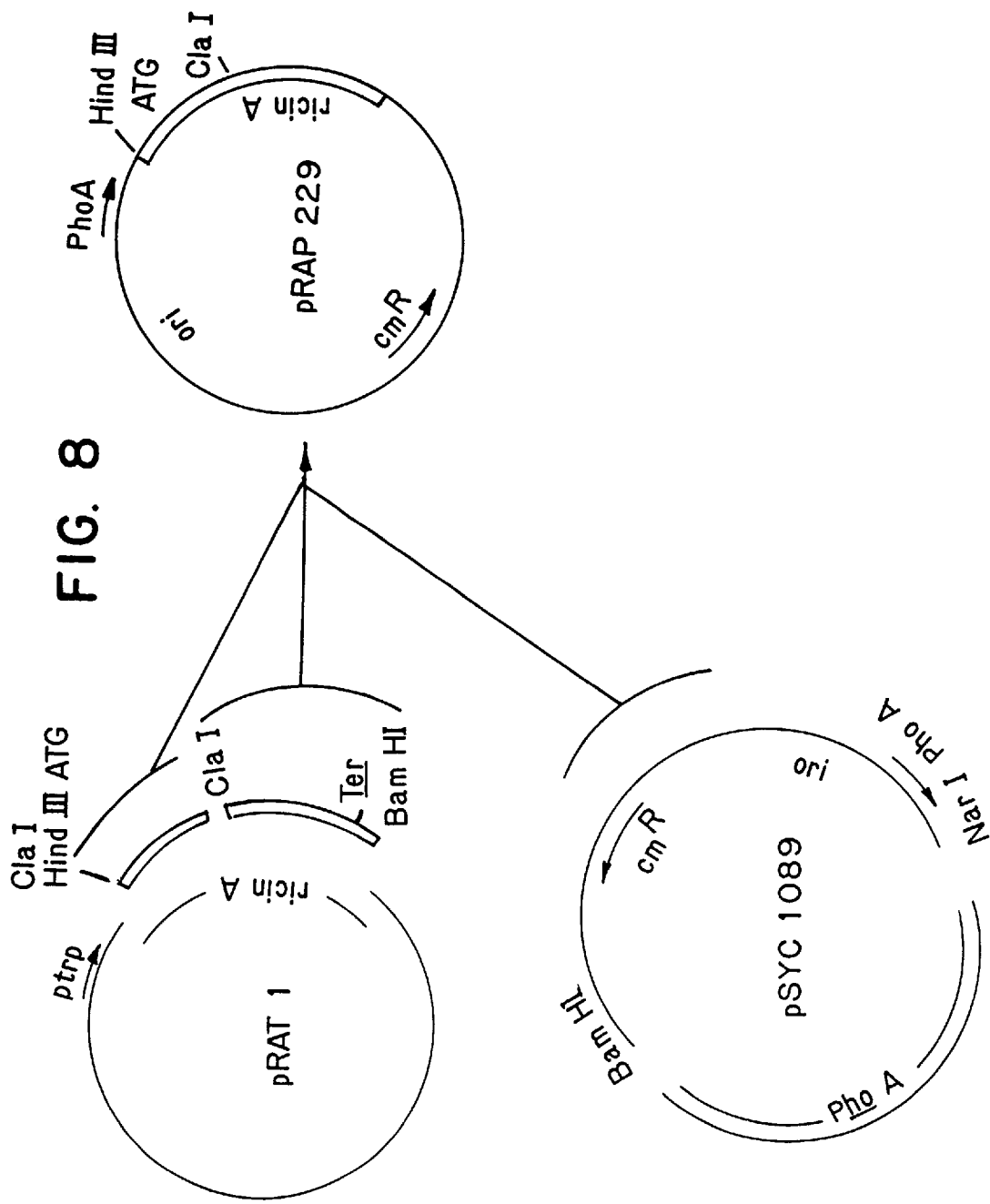
FIG. 8 shows the construction of pRAP229.
Figure 10:
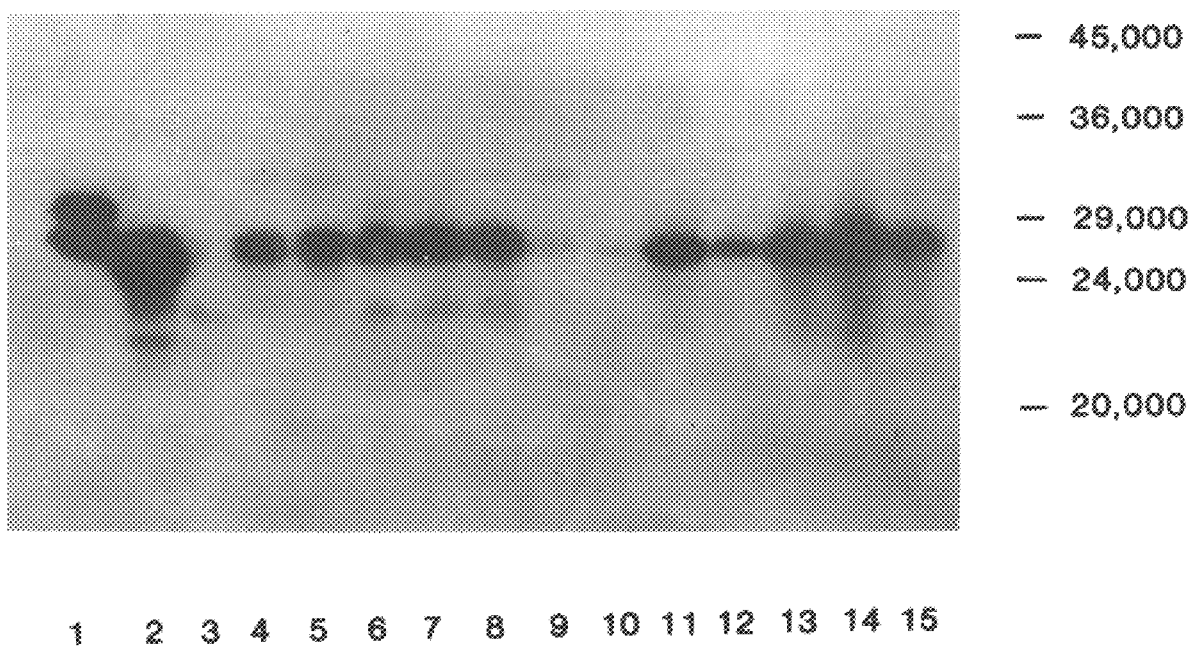
FIG. 10 shows the results of Western blots obtained using extracts of E. coli transformed with pRAP218 and pRAP229.
Figure 11:
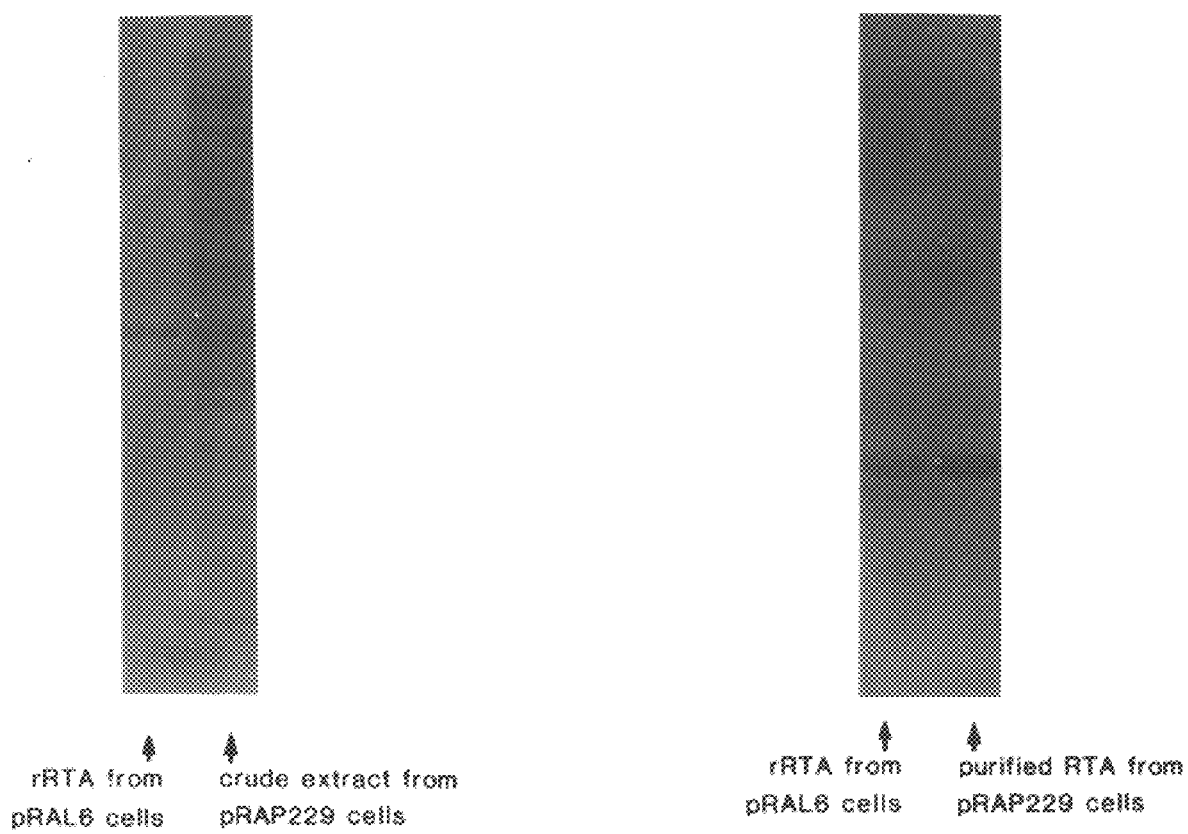
FIG. 11 shows comparative SDS-gels obtained from crude sonicate of pRAP229-transformed cells and from purified ricin A.

Three expression vectors were constructed. Two were vectors having the ricin A sequences in reading frame with leader and were constructed using pRAT1 and modified M13 subclones of pRA123 generally as shown in FIG. 7. A third expression vector typical of those of the invention, pRAP229 was constructed using coding sequences derived entirely from pRAT1 as shown in FIG. 8.

For the two in-frame vectors, pRAP218 and pRAP2210, the constructions employed a three-way ligation between (1) the large NarI/BamHI replicon-containing fragment of pSYC1089 which provides, in order, *B. thuringiensis*-positive retroregulator sequences, the chloramphenicol resistance marker, a compatible replicon, and the phoA promoter and leader sequences: (2) ClaI/BamHI-digested PRAT1 which provides a 500 bp fragment encoding the C-terminal portion of ricin A properly terminated; and (3) a 350 bp fragment upstream of the ClaI site in RF-DNA of appropriately modified M13/pRA123 subclones which contain the amino terminal encoding portion of ricin A.

For pRAP218, this latter fragment was derived from an M13/pRA123 subclone modified by site specific mutagenesis using:

```
                    MstI
5'-CATTAGAGGATAACTGCGCATTCCCCAAAC-3'
``` as primer. This places an MstI site at the N-terminus of the ricin A coding sequence. The desired 350 bp MstI/ClaI fragment from the modified pRA123, was ligated in three-way ligation mixture with ClaI/BamHI-digested pRAT1 and NarI/BamHI-digested pSYC1089 after the NarI site had been blunt-ended using *E. coli* DNA polymerase I (Klenow) in the presence of dCTP and dGTP. The resulting fusion contains an N-terminal alanine in place of the isoleucine of the ricin A sequence directly ligated in reading frame with the codon for the C-terminal alanine of the leader as shown in FIG. 9a.

pRAP2210 was constructed analogously except that the N-terminal sequences were provided as a 350 bp BglII/ClaI fragment from an M13 subclone modified using:

```
                    BglII
5'-CATTAGAGGATAACAAGATCTTCCCCAAAC-3'
``` as primer, which places a BglII site at the ricin A N-terminus. The BglII cleavage site was first partially repaired using dTTP, dATP and dGTP as substrates in the presence of Klenow and ligated in a mixture with ClaI/BamHI-digested pRAT1 and NarI/BamHI-digested pSYC1089 after the NarI cleavage site of the vector fragment had been partially repaired using dCTP in the presence of Klenow. The resulting ligation gave the sequence shown in FIG. 9b wherein the correct fusion contains the native N-terminal isoleucine codon fused in reading frame to the C-terminal alanine of the leader.

The corresponding expression vectors containing coding sequence for the precursor proteins were constructed exactly as described above except that the large NarI/BamHI replicon-containing fragment of pSYC1089 had had the BamHI site blunted with Klenow, and ClaI/XhoI (blunt) fragments from pRT3, pRT17 or pRT38, or from the modified M13 phage having, for example, the arg—arg encoding modification or the stop/start codon insertion, were used in place of the ClaI/BamHI fragment from pRAT. The resulting vectors are designated, generically, pR3P-218, pR17P-218, pR38P-218, pR3P-2210, etc.

The out-of-frame plasmid of the invention, pRAP229, for ricin A, was obtained by a similar three-way ligation except that the N-terminal sequence was provided by an approximately 350 bp ClaI/ClaI fragment from pRAT1 and the NarI site of the vector fragment was unrepaired. It is clear that the ricin A sequences could also have been, and might preferably be, prepared as a ClaI(partial)/BamHI-excised fragment from pRAT1. The resulting fusion (1) retains the start codon of the ricin A chain preceding the isoleucine residue; (2) is separated by 7 bp and thus out of reading frame relative to the leader sequence; (3) extends the phoA leader by the tripeptide Ile-SerOLeu; and (4) allows for termination of the leader sequence at a TGA codon out of frame with, but proximal to, the start codon of ricin A. The sequence at the pRAP229 fusion is shown in FIG. 9c. The corresponding vectors for the precursors are designated pR3P-229, pR17P-229, and pR38P-229. pRAP229 was deposited at ATCC on 8 March 1985 and has accession no. 53408.

The out-of-frame plasmid of the invention, pRAP229. was obtained by a similar three-way ligation except that the N-terminal sequence was provided by an approximately 35G bp ClaI/ClaI fragment from PRAT1 and the NarI site of the vector fragment was unrepaired. It is clear that the ricin A sequences could also have been, and might preferably be, prepared as a ClaI(partial)/BamHI-excised fragment from pRAT1. The resulting fusion (1) retains the start codon of the ricin A chain preceding the isoleucine residue; (2) is separated by 7 bp and thus out of reading frame relative to the leader sequence; (3) extends the phoA leader by the tripeptide Ile-Ser-Leu; and (4) allows for termination of the leader sequence at a TGA codon out of frame with, but proximal to, the start codon of ricin A. The sequence at the pRAP229 fusion is shown in FIG. 9c. pRAP229 was deposited-at ATCC on Mar. 8, 1985 and has accession no. 53408.

The methods described in this paragraph with respect to soluble ricin A produced in MM294 using an out of frame phoA leader may also be employed to extract soluble ricin A produces in MM294 under trp promoter control, such as in PRAT1. Comparable recoveries of ricin A are obtained. Where the extraction is conducted at a pH greater than 8, ricin A yields are in the range of 6–8% of total cell protein. This yield is greater than that set forth in ¶D.5 for pRAT1, where extraction is conducted under different conditions. Corresponding modification of extraction conditions for ricin A produced under $P_L$ control in MC1000, however, does not result in solubilization.

D.6.c. Production of Soluble Ricin A in *E. coli* pRAP218, pRAP2210, and pRAP229 were transformed into *E. coli* MM294 and the transformed cultures were grown under conditions similar to those described by Michaelis, et al, *J Bact* (1983) 154:356–365. The cells were induced by lowering the exogenous phosphate concentration and maintaining the cultures for 16–17 hr.

The cells were harvested, and whole cell extracts prepared by sonication in the absence of detergent were assayed for expression using Western blot employing rabbit antisera to native ricin A. The results are shown in FIG. 10 for pRAP218 and for pRAP229. (The results for pRAP2210 were exactly analogous to those for pRAP218.)

(One indication that a protein produced in *E. coli* may reside in the periplasmic space and is thus "secreted" is that it can be released by an osmotic shock. This test was performed essentially as described by Nassal and Heppel, *J Biol Chem* (1966) 241:3055–3062. Briefly, pellets of induced cell cultures are suspended to a density of approximately $7\times10^9$ cells/ml in buffer containing 50 mM Tris, pH 7.4, 2.5 mM EDTA, and 20% (w/v) sucrose, and kept at room temperature for 10 minutes. The cells are then pelleted and resuspended in ice-cold water and left on ice for 10 minutes. After centrifugation, the supernatant, referred to as the osmotic shockate, and the pellet, referred to as the osmotic cell pellet, are assayed as herein described.)

In FIG. 10, lanes 1 and 2 represent native and recombinant ricin, respectively. (The recombinant ricin was produced using pRAL6-transformed *E. coli* MM294, and the whole cell extract prepared by sonication was subjected to analysis.) In lane 1, the two forms of the native protein, $A_1$ and $A_2$, which differ in the extent of glycosylation, are clearly apparent. In lane 2, the large smeared spot of recombinant ricin A is an artifact resulting from overloading of the gel; it migrates, however, at the appropriate molecular weight (28 kD) for non-glycosylated ricin A. Lanes 3–8 represent extracts of induced pRAP218 cultures. Lane 3, the osmotic shockate shows the absence of ricin A protein in the periplasm. Lane 4, which is a shockate pellet, suggests that the protein resides intracellularly, or at least is associated with cellular structural components. Lanes 5, 6, and 7 are various fractions of the 3 min sonicates indicating a distribution of the protein through the fractions of the sonicate. Lane 5 is the low speed pellet; lane 6 the low speed supernatant; lane 7 the 100,000× g supernatant. Lane 8 corresponds to a 3 min sonication plus SDS to release all protein. Lane 9 is a control showing that uninduced transformants contain no ricin A.

Lanes 10–15 are the corresponding results from *E. coli* transformed with pRAP229. Again, the osmotic shockate (lane 10) contains no ricin A, while the intracellular components show the presence of the ricin A protein. It is important to note that in lane 14, the free ricin A protein is not removed from the supernatant by 100,000× g centrifugation. The presence of ricin A in pellet fractions is due to inefficient extraction of ricin A from membranes or other associated materials.

Estimation of quantities of materials present in non-blotted Coomassie-stained polyacrylamide gels show that for the in-frame plasmids, pRAP218 and pRAP 2210, the production is approximately 1–2% of total cell protein, and that the ricin A is approximately equally distributed between processed (28 kD) and unprocessed (30 kD) protein. For pRAP229, however, only molecular weight 28 kD is obtained, and this comprises at least 5–6% of total cell protein.

The corresponding precursor proteins are obtained from the analogous, for example, pR3P-218, pR17P-2210 and pR38P-229 transformants. If the modified precursor encoding DNA is employed, the trypsin-cleavable precursor or activated protein is produced.

The purified product from pRAP229 transformants was analyzed by NH2 terminal sequencing. This analysis shows that approximately 33% of the sequenceable protein is N-terminated by methionine; the remainder by isoleucine. (N-Formyl methionine-preceded peptides cannot be sequenced.)

NH2-terminal sequencing was carried out using an Applied Biosystems model 470A gas-phase sequencer which had been modified to eliminate the vacuum system The Applied Biosystems 02NVAC program was employed, using reagents and solvents supplied by the manufacturer The PTH-amino acid derivatives which were formed in the instrument by automatic conversion with 25% aqueous trifluoroacetic acid were identified using reverse-phase HPLC The HPLC system consisted of a Waters WISP sample injector, two Beckman model 112 pumps, a Beckman model 421 controller, an Altex 4.6 mm×15 cm Ultrasphere-ODS column, two Beckman model 160 detectors in tandem, set to 254 nm and 313 nm, respectively, a Kipp and Zonen two channel recorder and a Spectra-Physics model SP4100 computing integrator. PTH-amino acids were eluted with a gradient of acetonitrile:methanol (1:1) in 25 mM sodium acetate, pH 4.25.

D.6.d. Purification of Ricin A

To obtain sufficient ricin A protein for purification, cells were grown in a 10 liter fermenter and induced by depletion of phosphate concentration. The cells were grown in a medium which contained an autoclaved solution of 100 mM ammonium sulfate, 5 mM $KH_2$ $PO_4$, 1 mM sodium citrate, and 1 mM TK-9 which was supplemented with the following sterile additions: 3 mM $MgSO_4$, 5 g/l glucose, 20 mg/l thiamine hydrochloride, 72 $\mu$M ferrous sulfate, and 25 mg/l chloramphenicol. Inoculation was at 1 mg dry weight per liter from shake flasks of the transformants grown in a mineral salts/glucose medium.

After inoculation, the temperature of the fermenter was kept at 37° C., and the pH controlled to 6.8 by addition of KOH and coupled glucose feed. Dissolved oxygen was controlled at 40% of air saturation. Induction occurred upon depletion of the phosphate at an $OD_{680}$ of approximately 20. The cells were harvested by centrifugation at low speed approximately 4–5 hr after apparent induction.

Forty grams wet weight of cells were sonicated in the presence of 100 ml buffer X (buffer X contains 0.1 M Tris, pH 8.5; 25 mM EDTA, 0.1% β-mercaptoethanol) containing 0.5 M NaCl. After 30 minutes of sonication, 1 mg of phenyl methyl sulfonyl fluoride (PMSF) in 1 ml DMSO was added, and the sonicated mixture centrifuged for 30 minutes at 12,000× g. Note that the supernatant will still contain components which do not meet the herein defined criteria of solubility, as the centrifugation speed is relatively low.

The supernatant, which was not completely clarified, was loaded onto a phenylsepharose (Pharmacia, Ltd) column having a bed volume of 200 ml which had been equilibrated with phosphate-buffered saline (PBS), pH 7. The column was chased with 1 bed volume PBS, and then the protein eluted with a 0–50% propylene glycol gradient in PBS. Fractions were assayed by subjecting them to SDS gel electrophoresis and staining with Coomassie blue, using migration of previously authenticated ricin A purified from pRAL6 transformants to identify the desired bands. Recombinant ricin A eluted from the column at approximately 15% propylene glycol and the ricin A-containing fractions were pooled and diluted 10 times into buffer Y (20 mM sodium acetate, pH 5.5; 1 mM EDTA, 0.1% β-mercaptoethanol) for the succeeding purification steps.

This ricin A was soluble by the criteria herein defined. Control experiments without the use of phenyl sepharose yielded a soluble product, but immunoprecipitable ricin A remained associated with larger fragments which came down in the pellet during centrifugation. In addition, the yield of ricin A defined as soluble is greatly improved using phenyl sepharose as an adsorbent in the purification process.

The pooled fractions were applied onto a carboxymethyl sepharose column having a 200 ml bed volume which had been preequilibrated with buffer Y. Fractions were eluted with a 100–250 mM NaCl gradient in buffer Y, and the fractions were assayed using SDS gel/Coomassie blue staining, as above. The ricin A fractions eluted at approximately 150 mM NaCl and provided ricin A of approximately 95% purity, sufficient for research use.

The pooled ricin A-containing fractions were further purified by diluting ten-fold in buffer X and then applying the pool to a Cibacron Blue F3GA (Blue Trisacryl™, LKB) column. Fractions were eluted in 0–1 M NaCl in buffer X. Ricin A fractions were again identified by SDS gel/Coomassie blue staining, and shown to be eluted at approximately 0.5 M NaCl. These fractions showed a single band on SDS-PAGE, as shown in FIG. 11. FIG. 11 compares gels from the Trisacryl™, fractions with those from the soluble sonicate protein fraction. These fractions were pooled and could be used directly for conjugation to antibody. The material eluting from be Trisacryl™ column was active in the rabbit reticulocyte protein synthesis inhibition assay at approximately the same level as native ricin A (see below).

D.6.e. Immunotoxins Using Ricin A of the Invention

The pRAP229 products, purified as above, were used to prepare immunoconjugates with the monoclonal antibody 454A12. an immunoglobulin specific for the human transferrin receptor, and to the anti-breast monoclonal 280D11. Conjugates were prepared by two general methods, using iminothiolane or SPDP as linkers.

To form the conjugates, the procedures described by Bjorn, M. J., et al, *Biochim Biophys Acta* (1984) 790:154–163, were used. Briefly, breast monoclonal antibody 280D11, anti-transferrin receptor 454A12 or other desired antibodies were first derivatized with SPDP, and used to form disulfide links to the free cysteine sulfhydryls of ricin A. A 10–20 fold molar excess of SPDP was added to a solution containing 20 mg/ml of antibody in PBS and incubated at room temperature for 1 hr, and then dialyzed against PBS to remove unreacted SPDP. It was calculated that approximately 2–5 pyridyl-disulfide moieties were introduced into each antibody using this procedure. To complete the conjugation, solutions of ricin A containing 1–2 mg/ml which had been stored in reducing agent in 4° C. was passed over a Sephadex G-25 column equilibrated in PBS to remove the reducing agent, and the ricin A was mixed with derivatized antibody in 2–4 molar excess cytotoxic portion. Conjugation was confirmed by spectrophotometric determination of released pyridine-2-thiol and by SDS-PAGE.

In an alternative procedure, the appropriate monoclonal antibody (>30 mg/ml) was dialyzed against 100 volumes of 100 mM sodium phosphate, pH 8, 1 mM EDTA (P-EDTA) at 4° C. The antibody solution was brought to 1 mM 5,5'-dithiobis(2-nitrobenzoic acid) (DNTB), and then 2.5 equivalents of 2-iminothiolane (10 mM stock solution in water) were added. The reaction was allowed to proceed for 24 hours at 0° C. The number of thiols introduced by 2-iminothiolane and subsequently blocked by DTNB was determined spectrophotometrically by thionitrobenzoate release (extinction coefficient, 13.600/M at 412 nm). Excess 2-iminothiolane and DTNB were removed by dialysis against 3×100 volumes of P-EDTA at 4° C. The ricin A to be conjugated (>10 mg/ml) was dialyzed against 100 volumes of P-EDTA at 4° C. and the number of free thiols/ricin A determined spectrophotometrically using DTNB. The coupling of antibody and ricin A was effected by addition of a 1.2-fold excess of ricin A free thiols over antibody blocked thiols. The reaction was continuously monitored at 412 nm and was complete within 2 hours.

Conjugates were prepared using the soluble ricin A of the invention as well as using recombinant (pRAL6) ricin A, which is soluble only in detergent, and native ricin A. Immunotoxins can be tested in in vitro and in vivo cytotoxicity assays as described below.

For the assays, some of the immunotoxins were first purified. It was not possible to purify the immunoconjugates resulting from recombinant (pRAL6) ricin A, which were also soluble only in detergent. The conjugates of soluble ricin A of the invention and of native ricin A were first purified using a combination of fractionation on Blue Trisacryl™, and sizing on ACA-44. The original mixture, which contains free antibody, free ricin A, and the conjugate was first subjected to treatment with Blue Trisacryl™, which has an affinity for both ricin A and its conjugates. The mixture eluted from the column containing ricin A and ricin A conjugate was then subjected to size fractionation using ACA-44 to separate the unconjugated ricin A. The resulting conjugates were approximately >95% pure, when used in the assays below.

The in vitro assay followed the protocol set forth in Bjorn, et al (supra). In a typical protocol, human breast tumor cells (MCF-7) were seeded in 8 ml glass vials and dilutions of the immunoconjugates were added. Following incubation for 22 hrs at 37° C., the medium was removed and replaced with 0.5 ml medium lacking unlabeled methionine, but supplemented with 1 μCi of $^{35}S$ methionine. Following a 2-hr pulse, the medium was aspirated, the monolayer was washed twice with 10% trichloroacetic acid containing 1 mg/ml methionine and the vials were dried Following the addition of 3 ml of 4a20™ scintillation fluid (Research Products International Corporation) containing 20% (v/v) Triton X-100, the vials were counted. Toxicity was expressed as the concentration of protein required to inhibit protein synthesis by 50% ($TCID_{50}$).

In the in vivo assay, animals which had been implanted with tumors are used as subjects, and conjugates are injected to evaluate their effort on tumor growth. The results can be computed as % growth of tumors in experimental animals as compared to control.

Ricin A and its conjugates were also tested for toxicity by injection IV into Balb/C mice. $LD_{50}$ values were determined for conjugates both of the recombinant soluble ricin A of the invention and for native ricin A. Toxicity could not be determined for conjugates prepared from the insoluble recombinant (pRAL6) ricin A since these conjugates were unavailable in sufficient amounts, could not be purified, and contained detergents.

The results of the tests with regard to enzymatic activity, as well as of the foregoing in vitro and toxicity tests are shown below in Table 1.

As shown in Table 1, the enzymatic activity refers to the amount of ricin A in ng/ml required to give 50% inhibition of protein synthesis in the commercially available rabbit reticulocyte in vitro translation system.

Toxicity was computed as LD50 values obtained from a single injection IV of ricin A into Balb/C mice.

Cytoxocity was measured in vitro using immunotoxins with the ricin A proteins prepared as described above. Controls using either unconjugated native ricin A or pRAP229 ricin A showed cytotoxicity of approximately 20 nM.

The assay procedures were as described above. MCF-7 was used as sensitive cell line, and the results tabulated are the concentrations in nM of the conjugate able to elicit 50% killing of the sensitive cell line. Control non-sensitive cell lines, for example, CC95 typically showed $TCID_{50}$ values with the immunoconjugates of this assay of more than 100 nM.

TABLE 1

Representative Biological Activity
Comparison of Ricin A from pRAP229 and Native Ricin A

| | native ricin A | pRAP229 ricin A |
|---|---|---|
| Enzymatic | 1.76 ng/ml | 0.76 ng/ml |
| Activity | 1.78 ng/ml | 1.58 ng/ml |
| Toxicity $LD_{50}$ | 350 $\mu$g | 340 $\mu$g |
| Cytotoxicity of Immunoconjugates against MCF-7 | | |
| Mab 454A12 | 0.01 nM | 0.02 nM |
| Mab 280D11 | 0.1 nM | 0.4 nM |
| | 0.08 nM | |

The soluble pRAP229 ricin A of the invention shows comparable properties within experimental error to those of native ricin A, including enzymatic activity and formation of specifically cytotoxic conjugates. Preliminary results in in vivo assays suggest that the immunoconjugates formed with soluble pRAP229 ricin A are comparable to those formed with native ricin A in their ability to inhibit tumor growth.

D.7. Preparation of pRTB704 pRTB704 is CMCC number 1951 and was deposited with ATCC on 14 September 1984. pRTB704 is an expression plasmid having the ricin B sequence under the control of the $P_L$ promoter $N_{RBS}$. It is constructed from pRTB601, which contains the ricin B coding sequence and pFC5 which contains the $P_LN_{RBS}$. pFC5 is deposited with ATCC, accession no. 39864. To construct pRTB704, pRTB601 was digested with HindIII to excise the ricin B coding sequence, treated with FnuDII to destroy the $Amp^R$ region of the vector, and ligated using a T4 DNA ligase with a HindIII digest of pFC5. The mixture was transformed into *E. coli* MM294 and AmpR selected; the correct construction was confirmed by sequencing.

pRTB601

The polyA mRNA prepared as in ¶D.1 was used to obtain a cDNA library as follows: A portion of the polyA RNA was treated under appropriate buffer conditions with reverse transcriptase and then treated with base to destroy the remaining mRNA. The resulting single-stranded cDNA was repaired using *E. coli* Polymerase I (Klenow fragment) in the presence of the 4 dNTPs and the resulting "hairpin" then ligated using T4 ligase to a SalI linker (obtained from New England BioLabs). After treating with S1 nuclease and repairing with Klenow, the blunt end was ligated to an EcoRI linker using $T_4$ ligase. After then digesting with EcoRI and SalI, the resulting double-stranded CDNA fragments, which are bounded by EcoRI and SalI restriction sites, were ligated into a EcoRI/SalI digested, BAP treated preparation of pUC13 obtained and freely available from J. Messing, the University of Minnesota. pUC13 is a modification of pBR322 capable of conferring Amp resistance ($Amp^R$), and bearing a lac promoter control sequence upstream of linkers bearing convenient restriction sites, including EcoRI and PstI sites downstream from the SalI site used in the insertion; sites which are identical to those found in the analogous M13 phage cloning vectors. The resulting ligation mixture was used to transform *E. coli* MM294, and $Amp^R$ strains selected.

Successful colonies were transferred onto nitrocellulose plates, and probed using the procedure of Grunstein & Hogness (supra), with the mixture of 16 synthetic oligonucleotides $$5'\ CC\binom{A}{G}TC\binom{A}{G}TT\binom{C}{T}TT\binom{A}{G}AACATCC\ 3'$$

which is kinased with $^{32}P$. This mixture represents the anti-sense strand complementary to the codons for the amino acid sequence Trp-Met-Phe-Lys-Asn-Asp-Gly. Of about 5000 colonies probed about 1% were found which hybridized to the probe. Plasmids were isolated from several representations of these colonies, and analyzed by restriction analysis and Maxam-Gilnert sequencing. Three plasmids, pRTB4, pRTBS, and pRTA115 were sequenced in the insert region, and the results are shown in FIG. 4.

The amino acid sequence deduced from the pRTB5 base sequence shows a high level of correspondence to ricin B, although some discrepancies exist. These are due to possible errors in the published sequence and to varietal differences in the ricin B proteins represented. The entire coding sequence for ricin B is present in pRT5 except for codons for the first 11 amino acids. pRTB5 was used as the source of the bulk of the coding sequence in the expression vectors. The pRTA115 insert contains the upstream coding, regions of the ricin B gene. Although pRTA115 is believed associated with the RCA precursor protein, the amino acid sequence deduced from pRTA115 for RCA matches that of ricin B for the 11 amino acids needed to complete the N-terminus. These sequences were therefore used as models for the construction of oligonucleotides encoding the missing 11 N-terminus codons and also permit the deduction of the amino acid sequence of the 12 amino acid peptide in the single peptide precursor of RCA and, presumably, of ricin A and B.

The coding sequences of pRTB5 were disposed so as not to be expressible under the control of the lac promoter as inserted into pUC13. Therefore, pRTB5 was cut with EcoRI and PstI and the vector cleaved into several fragments with BstNI. The insert fragment was ligated under standard conditions using T4 ligase with an EcoRI/PstI digest of pUC8, another modified pBR322 vector obtained from and freely available from Messing, J., at the University of Minnesota. pUC8 has EcoRI and PstI sites which place an EcoRI/PstI insert under lac promoter control as a fusion protein with the initial 5–8 amino acids of β-galactosidase. It also contains a HindIII site immediately downstream from the PstI site. The ligation mixture was transformed into *E. coli* MM294, and transformants selected for ampicillin resistance. Plasmid DNA was isolated from successful transformants in several colonies, and analyzed by restriction site mapping. Colonies showing the appropriate restriction patterns were selected. One colony, designated pRTB151, was tested for expression of the gene for the fusion protein. On Western Blot no protein band corresponding to the desired molecular weight was found, although cross-reacting proteins were produced. It was assumed that the reading frame might be improper, since this plasmid was designed to have the β-galactosidase and ricin B sequences in different phases.

Ten μg of pRTB151 DNA was digested to completion with EcoRI, dissolved in 60 μl S1 buffer and digested for 4 min at room temperature under conditions which remove about 1 base pair of duplex DNA per min. DNA recovered from the foregoing buffer was dissolved in 60 μl exonuclease III buffer and digested for 4 min at room temperature. Subsequent analysis showed that the plasmid DNA had lost approximately 120 bp from each 3' end, leaving 5' ends available for hybridization. DNA recovered from the Exonuclease III buffer was dissolved in 50 μl water and 20 μl used in the ligation/repair reaction below.

Thus, 20 μl sample (2 pmoles) was mixed with pmoles each of the synthetic oligonucleotides:

5'- GACCATGATAAGCTTATGGCTGATGTTTGTATGGA
TCC                                                              Oligo 2 and

HindIII 3'TACCTAGGACTCGGGTATCACGCATAGCA
TCC-5'                                                           Oligo 1 which have complementary sequences as shown, and wherein Oligo-2 encodes a HindIII site upstream of an ATG start codon as shown in FIG. 5a. The 5' end of Oligo-1 is complementary to 15 bases at the 5' end of the pRTB151 cDNA sequence as there shown and is complementary to the contiguous missing codons of the ricin B sequence. The 5' end of Oligo-2 is complementary to the 5' sticky end of the vector residue of the exonuclease III treated pRTB151.

The mixture was heated to 600 for 5 min in order to denature completely complementation of single-stranded DNA, cooled to 37° for 5 min to hybridized complementary strands, and then chilled on ice. The solution was brought to polymerase I (Klenow) buffer conditions and reacted for 2 hr at 12° in the presence of the 50 μM each of the 4 dNTPs, 0.1 mM NAD, 0.3 units/μl Klenow, and 0.08 units/μl $E.\ coli$ DNA ligase. The ligation mixture was used directly to transform competent $E.\ coli$ MM294 and several thousand $Amp^R$ colonies found. Several hundred of these were replicated and grown on nitrocellulose filters and subjected to standard colony hybridization using $P^{32}$ kinased Oligo-2 as probe. Two clones which hybridized with the probe were analyzed by restriction analysis and sequenced, and a correct construction designated pRTB601. pRTB601 thus contains the ricin B coding sequence as a HindIII cassette. The upstream HindIII site is introduced immediately upstream of the ATG codon in Oligo-2; the downstream HindIII site arises from the pUCB vector plasmid.

The following plasmids have been deposited at the American Type Culture Collection, Rockville, Md., U.S.A. (ATCC) under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such strains is not to be construed as a license to practice the invention in contravention of the rights granted under the authority of any government in accordance with its patent laws.

The deposited plasmids have been assigned the indicated ATCC deposit numbers. The plasmids have also been deposited with the Master Culture Collection (CMCC) of Cetus Corporation, Emeryville, Calif.; U.S.A., the assignee of the present application, and assigned the indicated CMCC deposit numbers:

| Plasmid and Host | CMCC Deposit No. | ATCC Deposit No. | Date of ATCC Deposit |
|---|---|---|---|
| pRA123/ | 2108 | 39799 | 17 August 1984 |
| pRAL6/MC1000λ | 2114 | 39833 | 4 September 1984 |
| pRTB704/MC1000λ | 1951 | 39865 | 14 September 1984 |
| pFC5/MC1000λ | 1935 | 39864 | 14 September 1984 |
| pRAP229 | 2218 | 53408 | 8 March 1985 |
| pTRP3 | 1731 | 39946 | 18 December 1984 |
| pPLOP | 2118 | 39947 | 18 December 1984 |
| pRT3 | 2409 | | 7 March 1986 |
| pRTI7 | 2411 | | 7 March 1986 |
| pRT38 | 2410 | | 7 March 1986 |

The foregoing written specification is considered to be sufficient to enable one skilled in the art to practice the invention. The deposit of materials herein does not constitute an admission that the written description herein contained is inadequate to enable the practice of any aspect of the invention, including the best mode thereof, nor are they to be construed as limiting the scope of the claims to the specific illustrations which they represent.

What is claimed is:

1. A purified, isolated recombinant ricin E precursor polypeptide, free of other *Ricin communis* proteins, in which the A and B chains are linked by a linker polypeptide.

2. The ricin precursor polypeptide of claim 1 in which the A and B chains are linked by a non-native modified linker polypeptide comprising a cleavage site.

3. The ricin precursor polypeptide of claim 2 in which the A and B chains are linked by a trypsin cleavable linker.

4. The ricin E precursor polypeptide of claim 1 comprising the amino acid sequence of ricin E precursor set forth in FIGS. 14-1 and 14-2.

5. The ricin precursor polypeptide of claim 1 which is bacterially produced and unglycosylated.

6. A purified, isolated recombinant ricin E, free of other *Ricin communis* proteins.

7. The ricin of claim 6 which is bacterially produced and unglycosylated.

8. A purified, isolated recombinant B chain polypeptide of a ricin E, free of other *Ricin communis* proteins.

9. The B chain polypeptide of claim 8 which is bacterially produced and unglycosylated.

10. A purified, isolated recombinant RCA precursor polypeptide, free of other *Ricin communis* proteins, in which the A and B chains are linked by a linker polypeptide.

11. The RCA precursor polypeptide of claim 10 in which the A and B chains are linked by a non-native modified linker polypeptide comprising a cleavage site.

12. The RCA precursor polypeptide of claim 11 in which the A and B chains are linked by a trypsin cleavable linker.

13. The RCA precursor polypeptide of claim 10 which is bacterially produced and unglycosylated.

14. The RCA precursor polypeptide of claim 10 comprising the amino acid sequence of RCA precursor set forth in FIGS. 12-1 and 12-2.

15. A purified, isolated recombinant RCA, free of other *Ricin communis* proteins.

16. The purified, isolated recombinant RCA of claim 15 which is bacterially produced and unglycosylated.

17. A purified, isolated recombinant A chain polypeptide of an RCA, free of other *Ricin communis* proteins.

18. The A chain polypeptide of claim 17 which is bacterially produced and unglycosylated.

19. A purified, isolated recombinant B chain polypeptide of an RCA, free of other *Ricin communis* proteins.

20. The B chain polypeptide of claim 19 which is bacterially produced and unglycosylated.

21. A ricin E precursor polypeptide present within a non-*Ricin communis* host cell wherein the A and B chains are linked by a linker peptide.

22. A ricin E B-chain polypeptide present within a non-*Ricin communis* host cell.

23. An RCA precursor polypeptide present within a non-*Ricin communis* host cell wherein the A and B chains are linked by a linker peptide.

24. An A chain polypeptide of an RCA present within a non-*Ricin communis* host cell.

25. A B chain polypeptide of an RCA present within a non-*Ricin communis* host cell.

* * * * *